(12) United States Patent
Ochiai et al.

(10) Patent No.: US 7,524,985 B2
(45) Date of Patent: Apr. 28, 2009

(54) SACCHARIDE-MEASURING FLUORESCENT MONOMER, SACCHARIDE-MEASURING FLUORESCENT SENSOR SUBSTANCE, AND IMPLANTABLE, SACCHARIDE-MEASURING SENSOR

(75) Inventors: Shouji Ochiai, Nakai-machi (JP); Tetsuro Kawanishi, Nakai-machi (JP); Atsushi Matsumoto, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/890,518

(22) Filed: Aug. 7, 2007

(65) Prior Publication Data

US 2008/0021236 A1 Jan. 24, 2008

Related U.S. Application Data

(62) Division of application No. 11/187,821, filed on Jul. 25, 2005.

(30) Foreign Application Priority Data

Jul. 23, 2004 (JP) ............... 2004-216535
Oct. 14, 2004 (JP) ............... 2004-299991

(51) Int. Cl.
*C07F 5/02* (2006.01)
(52) U.S. Cl. .......................... 562/7; 600/317
(58) Field of Classification Search ........ 600/317; 562/7
See application file for complete search history.

(56) References Cited

U.S. PATENT DOCUMENTS

| | | | |
|---|---|---|---|
| 5,503,770 A | 4/1996 | James et al. | |
| 6,002,954 A | 12/1999 | Van Antwerp et al. | |
| 6,011,984 A | 1/2000 | Van Antwerp et al. | |
| 6,304,766 B1 | 10/2001 | Colvin, Jr. et al. | |
| 6,319,540 B1 | 11/2001 | Van Antwerp et al. | |
| 6,330,464 B1 | 12/2001 | Colvin, Jr. et al. | |
| 6,682,938 B1 | 1/2004 | Satcher, Jr. et al. | |
| 6,794,195 B2 | 9/2004 | Colvin, Jr. | |
| 6,800,451 B2 * | 10/2004 | Daniloff et al. | 435/14 |
| 6,804,544 B2 | 10/2004 | Van Antwerp et al. | |
| 7,060,503 B2 * | 6/2006 | Colvin, Jr. | 436/95 |
| 7,078,554 B2 * | 7/2006 | Daniloff et al. | 558/288 |
| 7,450,980 B2 * | 11/2008 | Kawanishi | 600/317 |
| 2002/0039793 A1 | 4/2002 | Colvin, Jr. | |
| 2002/0090734 A1 | 7/2002 | Daniloff et al. | |
| 2002/0127626 A1 | 9/2002 | Daniloff et al. | |
| 2002/0197724 A1 | 12/2002 | Noronha et al. | |

FOREIGN PATENT DOCUMENTS

| | | |
|---|---|---|
| JP | 5-245198 A | 9/1993 |
| JP | 8-53467 A | 2/1996 |
| WO | 02/12251 A1 | 2/2002 |
| WO | 03/042698 A1 | 5/2003 |

OTHER PUBLICATIONS

Tony D. James et al, "Novel Saccharide-Photoinduced Electron Transfer Sensors Based on the Interaction of Boronic Acid and Amine", *J. Am. Chem. Soc.*, vol. 117, No. 35 (1995), American Chemical Society, pp. 8982-8987.
Masayuki Takeuchi et al, "Fluorescence and CD Spectroscopic Sugar Sensing by a Cyanine-appended Diboronic Acid Probe", *Tetrahedron*, vol. 52, No. 4 (1996), Elsevier Science Ltd., pp. 1195-1204.
Susumu Arimori et al, "Modular fluorescence sensors for saccharides", *Chemical Communications*, vol. 18, (2001), Royal Society of Great Britain, pp. 1836-1837.

* cited by examiner

*Primary Examiner*—Sikarl A Witherspoon
*Assistant Examiner*—Chukwuma O Nwaonicha
(74) *Attorney, Agent, or Firm*—Buchanan, Ingersoll & Rooney PC

(57) ABSTRACT

A fluorescent monomer compound represented by the following formula (1) is provided:

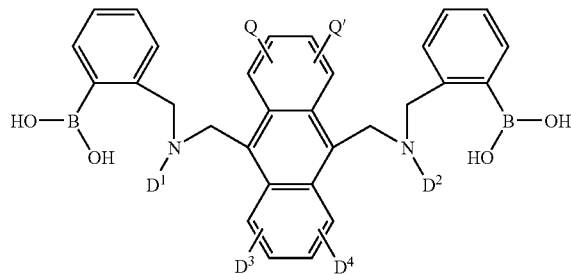

formula (1)

wherein Q, Q' and $D^3$ may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups; and $D^1$, $D^2$ and $D^4$ each represent a substituent, wherein at least one of $D^1$, $D^2$ and $D^4$ is a substituent group comprising a vinyl group at an end thereof, and wherein the substituent group comprising a vinyl group at an end thereof enables the fluorescent monomer compound to be soluble in water.

5 Claims, 10 Drawing Sheets

F—AAm

SACCHARIDE-MEASURING FLUORESCENT MONOMER, SACCHARIDE-MEASURING FLUORESCENT SENSOR SUBSTANCE, AND IMPLANTABLE, SACCHARIDE-MEASURING SENSOR

CROSS-REFERENCE TO RELATED APPLICATIONS

This application is a divisional of prior application Ser. No. 11/187,821, filed Jul. 25, 2005, the entire contents of which are hereby incorporated by reference, which in turn claims priority under 35 U.S.C. § 119 to Japanese Patent Application Nos. 2004-216535 filed Jul. 23, 2004 and 2004-299991 filed Oct. 14, 2004.

BACKGROUND OF THE INVENTION

This invention relates to fluorescent monomer compounds, fluorescence sensor substances, their production process, and implantable, saccharide-measuring sensors making use of them. These fluorescent monomer compounds, fluorescence sensor substances and implantable, saccharide-measuring sensors are excellent in the ability to detect saccharides.

DESCRIPTION OF THE RELATED ART

Implantable sensors are useful for the progress observation of morbid conditions, the monitoring of therapeutic effects, and the like purposes in various diseases, and their developments have become one of active research fields in recent years. Especially in the treatment of diabetes, the control of blood sugar by continuous blood-sugar measurement is considered to contribute to a retardation in the progress of morbid conditions and a reduction in the development of complications.

For the self-control of blood sugar, many of current diabetics collect blood samples by punctures of their fingers or the like, and feed them to blood sugar meters to read measurement data. However, this method involves problems of causing pain to patients and in simplicity and easiness, so that it may not be practical to perform more than several measurements in a day. Under the current circumstances, it is hence difficult to ascertain the trend of variations in blood sugar level through frequent measurements. For these reasons, implantable, continuous blood sugar meters are considered to have high utility.

On the other hand, technologies have been developed over many years for the continuous measurement of the in vivo glucose level. Such technologies include, for example, the measurement of a glucose level, which relies upon a change in fluorescence intensity by using a substance that reversibly reacts with glucose to emit fluorescence. As such a fluorescent substance, JP 8-53467 A discloses a fluorescence-emitting compound having a molecular structure that contains at least one phenylboronic acid moiety and at least one amine-providing nitrogen atom where the nitrogen atom is disposed in the vicinity of the phenylboronic acid moiety so as to interact intramolecularly with the boronic acid moiety. As the fluorophore, a naphtyl group, anthryl group or the like is used. Upon formation of a stable complex with a saccharide molecule via the phenylboronic acid moiety, the compound emits fluorescence.

As an indicator macromolecule for detecting the concentration of an analyte in an aqueous environment, WO 02/12251 A1 discloses a copolymer of a hydrophilic monomer and an excimer-forming polycyclic aromatic hydrocarbon such as an anthracene derivative. As the excimer-forming polycyclic aromatic hydrocarbon is not sufficient in water solubility, hydrophilic groups such as methacrylamide groups are introduced such that the concentration of an analyte can be detected even in an aqueous environment.

Further, U.S. Pat. No. 6,319,540 A1 discloses a process for directly immobilizing a fluorescent substance in a solid phase such as a plastic film to provide a fluorescence sensor. Employed in U.S. Pat. No. 6,319,540 A1 is a fluorescent substance formed of an atomic group, which has light emitting property, fluorescence emitting property and color producing property, only one phenylboronic acid moiety added to the atomic group.

However, the compound disclosed in JP 8-53467 A contains as a fluorophore a bulky hydrophobic moiety such as a naphthyl group or anthryl group, and therefore, its binding to a water-soluble saccharide is not easy. There is, accordingly, an outstanding desire for improvements in detection sensitivity. Further, the compound disclosed in WO 02/12251 A1 is used as a solution in ethylene glycol upon conducting polymerization with a hydrophilic monomer such as methacrylic acid. The use of an organic solvent upon polymerization, however, has a potential problem in that a gel of such undesired properties as developing variations upon measurement in an aqueous solution may be obtained.

On the other hand, the direct immobilization of a fluorescent substance on a support material to use the fluorescent substance as a fluorescence sensor may result in the production of smaller signals because there is a limitation to the degree of freedom of the fluorescent substance immobilized on the support material. Further, immobilization of the fluorescence substance at a high density may result in quenching. The ability of the fluorescent substance to detect a target substance may, therefore, be reduced compared with that of the same fluorescent substance before its immobilization.

SUMMARY OF THE INVENTION

The present invention can provide a fluorescent monomer compound excellent in the ability to detect a saccharide such as glucose, a fluorescence sensor substance, and a saccharide-measuring sensor making use of the fluorescence sensor substance.

The present inventors studied in detail the states of binding of saccharides to saccharide-measuring fluorescent monomer compounds. As a result, it was found that the introduction of one or more hydrophilic groups, or the introduction of only one hydrophilic group, such as one comprising a polyalkylene or the like, to a hydrophobic moiety which emits fluorescence upon binding with a saccharide, makes it possible to promote the binding with the saccharide while maintaining the degree of freedom of the hydrophobic moiety and also that the copolymerization of the fluorescent monomer compound with (meth)acrylamide makes it possible to perform the measurement of a saccharide without a reduction in detection sensitivity even in an aqueous solution such as blood or a body fluid even when the resulting copolymer is immobilized on a support material. Based on these findings, the present invention has been completed.

Saccharide-measuring fluorescent monomer compound, fluorescence sensor substance and detector layers according to the present invention are excellent in the ability to detect saccharides. Owing to their excellent ability to detect saccharides in body fluids, these fluorescent monomer compound, fluorescence sensor substance and detector layers can provide fluorescence sensors which can withstand their long-term implantation.

The above and other objects, features and advantages of the present invention will become clear from the following description of preferred embodiments.

DETAILED DESCRIPTION OF PREFERRED EMBODIMENTS

Figure 1:
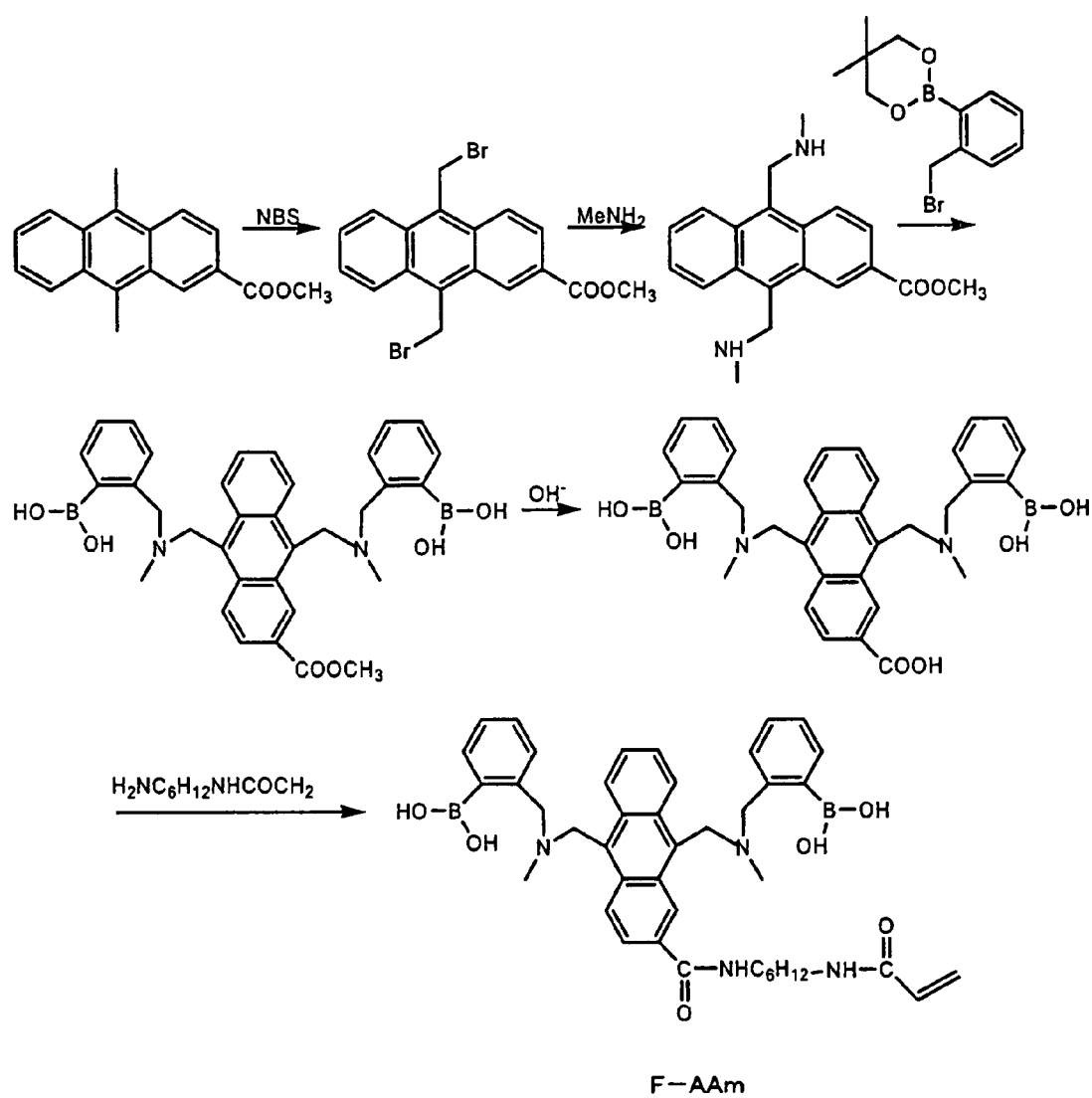
FIG. 1 is a diagram showing one example of a synthesis scheme for 9,10-bis[[N-methyl-N-(ortho-boronobenzyl)amino]methyl]anthracene-2-carboxylic acid-1-(6-acrylamido-n-hexyl)amide (F-AAm).

In a first aspect of the present invention, there is provided a fluorescent monomer compound represented by the following formula (1):

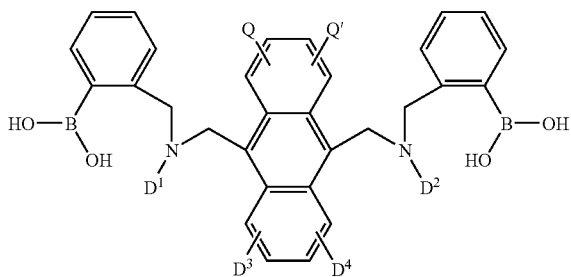

Formula (1)

wherein: Q, Q' and $D^3$ may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups, and preferably, Q and Q' may each be a hydrogen atom or an acetyl or nitro group; and at least one substituent selected from the group consisting of $D^1$, $D^2$ and $D^4$ is a substituent group which comprises a vinyl group at an end thereof, and wherein the substituent group comprising a vinyl group at an end thereof enables the fluorescent monomer compound to be soluble in water. The inclusion of a vinyl group at the end facilitates the polymerization of the fluorescent monomer compound itself, the polymerization with another polymerizable monomer, and the immobilization on the support material.

The expression "enables the fluorescent monomer compound to be soluble in water" as used herein means that the fluorescent monomer compound can be dissolved at a concentration of 1 mM or higher in water under conditions of 25° C. temperature and pH 7.0 without the presence of any organic solvent or solubilizer. As the substituent group that can enable the fluorescent monomer compound to be soluble in water, a substituent group represented by the below-described formula (2) or formula (3) can be mentioned preferably. Details of the substituent groups represented by the formula (2) or formula (3) will be described subsequently herein. More preferably, $D^1$, $D^2$, $D^3$ and $D^4$ can have meanings under the following definitions (i) or (ii):

(i) $D^1$ and $D^2$ may be the same or different and are each a substituted or unsubstituted alkyl group, $D^3$ is a hydrogen atom, and $D^4$ is a substituent group represented by the below-described formula (2). As the alkyl group, methyl, ethyl, propyl, butyl, pentyl or the like is preferred, with methyl or ethyl being more preferred.

(ii) $D^1$ and $D^2$ may be the same or different and are each a substituent group represented by the following formula (3), and $D^3$ and $D^4$ may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups. As the alkyl groups, those having 1 to 10 carbon atoms are preferred. Specific examples include methyl, ethyl, propyl, butyl and pentyl. Examples of the acyl groups include formyl, acetyl, propionyl, butyryl and isobutyryl. Examples of the oxyalkyl groups include methoxy and ethoxy. Examples of the halogen atoms include F, Cl, Br and I. Examples of the aminoalkyl groups include methylamino and ethylamino. Introduction of nitro, cyano and/or acyl groups as Q, Q', $D^3$ and $D^4$ can bring about an effect that contributes to the red-shift of fluorescence or the widening of the distance between an excitation wavelength peak and a fluorescence wavelength peak, thereby facilitating an analysis of the results of fluorometry.

When $D^1$, $D^2$, $D^3$ and $D^4$ have the meanings of the definition (ii) in the present invention, it is preferred that at least one of Q, Q', $D^3$ and $D^4$ is a substituent group selected from acetyl, carboxylate ester and cyano groups and the remainder(s) is(are) hydrogen atom(s).

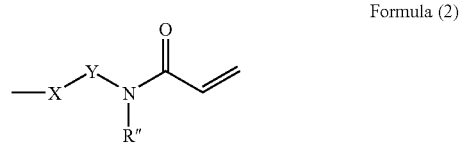

Formula (2)

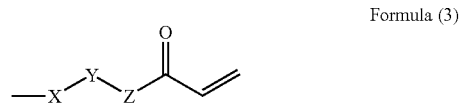

Formula (3)

A description will first be made of a case in which $D^1$, $D^2$, $D^3$ and $D^4$ have the meanings of the definition (i) in the formula (1).

In the definition (i), X is a substituent group selected from the group consisting of —COO—, —OCO—, —CH$_2$NR—, —CH$_2$S—, —CH$_2$O—, —NR—, —NRCO—, —CONR—, —SO$_2$NR—, —NRSO$_2$—, —O—, —S—, —SS—, —NRCOO—, —OCONR— and —CO—. Examples of the alkyl group include methyl, ethyl, propyl, butyl and pentyl. Preferred examples of X include —NRCO— and —CONR—.

In the definition (i), R" represents a hydrogen atom or a substituted or unsubstituted alkyl group. As the alkyl group, one having 1 to 10 carbon atoms is preferred, with one having 1 to 5 carbon atoms being more preferred. Specific examples include methyl, ethyl, propyl, butyl and pentyl.

In the definition (i), Y is a substituted or unsubstituted, divalent, organic residual group, and enables the fluorescent monomer compound to be soluble in water. The expression "enables the fluorescent monomer compound to be soluble in water" as used herein means that the fluorescent monomer compound can be dissolved at a concentration of 1 mM or higher in water under conditions of 25° C. temperature and pH 7.0 without the presence of any organic solvent or solubilizer. Preferred examples of Y include those containing one or more hydrophilic groups such as amino, carboxy, sulfo, nitro, amino, phosphate and/or hydroxyl groups; and those containing one or more hydrophilic linkages such as ether, amide and/or ester linkages in their structures.

Further, Y may preferably contain, in the organic residual group, a structure represented by the below-described formula (4) or (5). Y may additionally contain one or more other substituent groups and/or divalent, organic residual groups. In the formula (4) and formula (5), n can preferably be from 2 to 4, with 2 to 3 being more preferred; j can preferably be from 1 to 3, with 1 being more preferred; and m can preferably be from 20 to 150, with 40 to 120 being more preferred. Y' and Y" may be the same or different, and are each a hydrogen atom or alkyl group. As the alkyl group, one having 1 to 4 carbon atoms is preferred. Illustrative are methyl, ethyl, propyl and butyl. As Y' and Y", it is particularly preferred that Y' and Y" are each a hydrogen atom or that Y' is a hydrogen atom and Y" is an alkyl group having 1 to 4 carbon atoms, notably a methyl group.

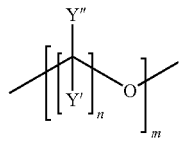

Formula (4)

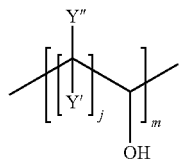

Formula (5)

Y can preferably have number of atoms of from 3 to 500, with 3 to 12 being more preferred.

A description will next be made of a case in which $D^1$, $D^2$, $D^3$ and $D^4$ have the meanings of the definition (ii) in the formula (1).

In the definition (ii), X represents a C1-C30 alkylene group containing at least one substituent group selected from the group consisting of —COO—, —OCO—, —CH$_2$NR—, —NR—, —NRCO—, —CONR—, —SO$_2$NR—, —NRSO$_2$—, —O—, —S—, —SS—, —NRCOO—, —OCONR— and —CO—. R represents a hydrogen atom or a substituted or unsubstituted alkyl group. The expression "alkylene group containing at last one substituent group" as used herein means an alkylene group containing at least one substituent group at an end thereof or an alkylene group containing at least one substituent group in the chain thereof. The carbon number of the alkylene group may be preferably from 1 to 30, more preferably from 3 to 12. Specific examples include propylene, hexylene and octylene. As the at least one substituent group contained in the alkylene group, —NRCO— or —CONR— is preferred. When R is an alkyl group, one having 1 to 10 carbon atoms being preferred, with 1 to 5 being more preferred. Specific examples include methyl, ethyl, propyl, butyl and pentyl. As R, a hydrogen atom is preferred.

In the definition (ii), Z represents —O— or —NR"—, and R" represents a hydrogen atom or a substituted or unsubstituted alkyl group. As the alkyl group, one having 1 to 10 carbon atoms is preferred, with one having 1 to 5 carbon atoms being more preferred. Specific examples include methyl, ethyl, propyl, butyl and pentyl. As Z, —O— is preferred.

In the definition (ii), Y is a substituted or unsubstituted, divalent, organic residual group, and enables the fluorescent monomer compound to be soluble in water. The expression "enables the fluorescent monomer compound to be soluble in water" as used herein means that the fluorescent monomer compound can be dissolved at a concentration of 1 mM or higher in water under conditions of 25° C. temperature and pH 7.0 without the presence of any organic solvent or solubilizer. Preferred examples of Y include those containing one or more hydrophilic groups such as amino, carboxy, sulfo, nitro, amino, phosphate and/or hydroxyl groups; and those containing one or more hydrophilic linkages such as ether, amide and/or ester linkages in their structures.

In the definition (ii), Y can preferably have a molecular weight of from 500 to 10,000, with 1,000 to 5,000 being more preferred.

Owing to the introduction of the hydrophilic chains Y as a characteristic feature of the present invention, the present invention can bring about advantageous effects such as, for example, those to be described below under (1), (2), (3) and (4).

(1) As the fluorescent monomer compound is enabled to be soluble in water, it is possible to efficiently conduct immobilization and a polymerization reaction upon forming a fluorescence sensor substance. Upon preparation of an acylamide gel, for example, polymerization is feasible using only water as a solvent, and one having high physical strength, stability and uniformity can be obtained. With a hydrophobic monomer compound, use of an organic solvent or the like is needed for its solubilization, and a gel of undesired properties may be obtained. (2) The introduction of the hydrophilic chains can modify the environment and mobility around phenylboronic acid moieties which interact with an analyte, thereby contributing to improvements in sensitivity, accuracy, response speed, and the selectivity to a saccharide as the analyte. (3) The hydrophilic chains can stabilize the fluorescence sensor substance in its entirety, for example, its polymerized structure. (4) As the fluorescent monomer compound can be reacted in water alone, its polymerization is feasible even on a support material susceptible to attacks by an organic solvent, for example, on an plate made of an acrylic resin or the like.

The fluorescent monomer compound according to the present invention is characterized in that Y is introduced via X into a compound for detecting a saccharide. This has made it possible to provide the fluorescent monomer compound with improved physical properties, stability, detection sensitivity, detection accuracy, and selectivity to the saccharide as the analyte. Described specifically, the introduction of hydrophilic groups represented by the formula (4) or formula (5) leads to an improvement in the degree of freedom at the phenylboronic acid moieties, which are contained in the fluorescent monomer compound, in an aqueous solution such as blood or a body fluid, thereby making it possible to promptly interact with a saccharide. As a consequence, the affinity to the saccharide can be increased to improve the detection sensitivity.

Especially in the case of the definition (i) in the formula (1), only one hydrophilic group has been introduced in a hydrophobic moiety which binds to a saccharide to emit fluorescence. Accordingly, the binding with the saccharide can be promoted while retaining a degree of freedom at the hydrophobic moiety.

It is known that, as described above, the fluorescent monomer compound according to the present invention is a phenylboronic acid derivative with an anthracene skeleton included therein and the anthracene skeleton acts as a fluorophore. When the phenylboronic acid moieties and a saccharide form stable complexes, fluorescence is emitted owing to the inclusion of the fluorophore. As the fluorescent monomer compound according to the present invention contains two phenylboronic acid moieties, it is excellent especially in the detection sensitivity to saccharides. It is to be noted that COCHCH$_2$ bonded with Z in the formula (3) has been introduced to bind the fluorescent monomer compound to a support material or the like such that the fluorescent monomer compound is prevented from dissolution in a body flood such as blood.

In the second aspect of the present invention, there is provided a saccharide-measuring fluorescence sensor substance comprising a copolymer of at least the following two compounds (I) and (II):

(I) a fluorescent monomer compound represented by the formula (1), and
(II) at least one hydrophilic, non-fluorescent, polymerizable monomer having a vinyl group.

To detect a saccharide, which is contained in an aqueous solution such as a blood or a body fluid, by using the fluorescent monomer compound, immobilization of the fluorescent monomer compound is needed to prevent the fluorescent monomer compound from being dissolved in or flowing out into the aqueous solution. When the fluorescent monomer compound is simply immobilized on a support material, however, the contact and binding between the fluorescent monomer compound and the saccharide is inhibited, leading to a reduction in detection sensitivity. In the present invention, the fluorescent monomer compound and the at least one hydrophilic, non-fluorescent, polymerizable monomer containing the vinyl group are, therefore, copolymerized to introduce and immobilize the hydrophilic polymerizable monomer in the fluorescent monomer compound so that the fluorescence sensor substance is formed. This has made it possible to make the fluorescent monomer compound insoluble while assuring high affinity between the fluorescent monomer compound and the saccharide.

Upon preparation of the fluorescence sensor substance, the above-mentioned at least one hydrophilic, non-fluorescent, polymerizable monomer having the vinyl group can be dissolved in water even at a concentration required for polymerization. When the fluorescence sensor substance is prepared in the form of a gel, for example, the gel can hence be obtained with such desired properties as scarcely developing variations in measurement data. Upon preparing the fluorescence sensor substance with the at least one hydrophilic, non-fluorescent, polymerizable monomer having the vinyl group, the concentration of the monomer in a reaction mixture can range preferably from 0.5 to 50 wt %, more preferably from 3 to 30 wt %.

As the at least one hydrophilic, non-fluorescent, polymerizable monomer having the vinyl group, a polymerizable monomer having an acrylic acid residual group or a polymerizable monomer having a (meth)acrylamide residual group can be preferably mentioned, with the polymerizable monomer having the (meth)acrylamide residual group being more preferred. The polymerizable monomer having the (meth)acrylamide residual group is excellent especially in water solubility and operation ease.

No particular limitation is imposed on the polymerizable monomer having an acrylic acid residual group insofar as the resulting polymer contains acryloyl groups in its structure. Examples can include 4-hydroxydibutyl acrylate, 2-hydroxyethyl acrylate, hydroxypropyl acrylate, methoxyethyl acrylate, polyethyleneglycol acrylate, and acrylic acid.

No particular limitation is imposed on the polymerizable monomer having the (meth)acrylamide residual group insofar as the resulting polymer contains acryloyl groups and amide linkages in its structure. Examples can include (meth)acrylamide and its derivatives. Illustrative are condensation products between (meth)acryloyl chloride and amino acids or compounds containing active amino groups, such as acrylamide, methacrylamide, N,N-dimethylacrylamide, N-tris-hydroxymethylacrylamide, N-hydroxymethylacrylamide, N-(n-butoxymethyl)acrylamide, N-acryloyl lysine, and N-acryloylhexamethylenediamine; and compounds represented by the following formula (6):

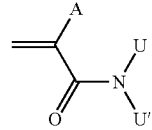

Formula (6)

In the formula (6), A is a hydrogen atom or a methyl group, and U and U' may be the same or different and are each a substituted or unsubstituted alkyl group. Examples of the alkyl group include methyl, ethyl, propyl, butyl, and pentyl.

The polymer, which comprises the polymerizable monomer with the (meth)acrylamide residual group contained therein, has high hydrophilicity so that, when bonded with the fluorescent monomer compound, the fluorophores which exist in the fluorescent monomer compound, contain the phenylboronic acid moieties and have strong hydrophobicity are incorporated in the highly hydrophilic structure. Even when a saccharide contained in blood or a body fluid is to be measured, water-soluble saccharide can, therefore, easily approach and bind to the fluorophores.

The molar ratio [(I):(II)] of the fluorescent monomer compound (I) to the polymerizable monomer containing the acrylamide residual group in the copolymer may be preferably from 1:10 to 1:4,000, more preferably from 1:50 to 1:4,000, especially preferably from 1:100 to 1:2,000 when $D^1$, $D^2$, $D^3$ and $D^4$ have the meanings of the definition (i) in the fluorescent monomer compound. A proportion of the fluorescent monomer compound (I) greater than that giving the molar ratio of 1:10 involves a potential problem that the degree of freedom may be lost due to the bulkiness of the hydrophobic moieties of the fluorescent monomer compound and the interaction with a saccharide may be reduced. A proportion of the fluorescent monomer compound (I) smaller than that giving the molar ratio of 1:4,000, on the other hand, may not be able to assure the absolutely-needed level of fluorescence intensity.

The molar ratio [(I):(II)] of the fluorescent monomer compound (I) to the polymerizable monomer containing the acrylamide residual group in the copolymer may be preferably from 1:50 to 1:6,000, more preferably from 1:150 to 1:3,000 when $D^1$, $D^2$, $D^3$ and $D^4$ have the meanings of the definition (ii) in the fluorescent monomer compound. A proportion of the fluorescent monomer compound (I) greater than that giving the molar ratio of 1:50 involves a potential problem that the degree of freedom may be lost due to the bulkiness of the hydrophobic moieties in the fluorescent monomer compound and the interaction with a saccharide may be reduced. A proportion of the fluorescent monomer compound (I) smaller than that giving the molar ratio of 1:6,000, on the other hand, may not be able to assure the absolutely-needed level of fluorescence intensity.

The weight average molecular weight of the fluorescence sensor substance composed of the above-described two components can be preferably from 50,000 to 500,000, more preferably from 100,000 to 300,000, as determined by GPC using a polyethylene oxide standard, when $D^1$, $D^2$, $D^3$ and $D^4$ have the meanings of the definition (i) in the fluorescent monomer compound.

The weight average molecular weight of the fluorescence sensor substance can be preferably from 50,000 to 750,000, more preferably from 150,000 to 450,000, as determined by GPC using a polyethylene oxide standard, when $D^1$, $D^2$, $D^3$ and $D^4$ have the meanings of the definition (ii) in the fluorescent monomer compound.

The fluorescence sensor substance according to the present invention may use one or more other components in addition to the fluorescent monomer compound and the polymerizable monomer containing the (meth)acrylamide residual group. Examples of such components include crosslinkable monomers, other crosslinkable components, cationic monomers cable of providing cations in water, anionic monomers capable of providing anions in water, and nonionic monomers containing no groups capable of liberating ions in water.

Examples of the crosslinkable monomers include a wide variety of those capable of introducing a three-dimensional crosslinked structure into the fluorescence sensor substance via polymerizable double bonds. Illustrative are divinyl compounds such as N,N'-methylene bis(meth)acrylamide, N,N'-(1,2-dihydroxyethylene)-bis(meth)acrylamide, diethylene glycol di(meth)acrylate, (poly)ethylene glycol di(meth)acrylate, triethylene glycol di(meth)acrylate, propylene glycol di(meth)acrylate, trimethylolpropane di(meth)acrylate, trimethylolpropane tri(meth)acrylate, pentaerythritol di(meth)acrylate, pentaerythritol tri(meth)acrylate, pentaerythritol tetra(meth)acrylate, (poly)propylene glycol di(meth)acrylate, glycerin tri(meth)acrylate, glycerin acrylate methacrylate, ethylene-oxide-modified trimethylolpropane tri(meth)acrylate, pentaerythritol tetra(meth)acrylate, and dipentaerythritol hexa(meth)acrylate, although they differ depending on the substituent groups in the fluorescence sensor substance to be used. Two or more of these crosslinkable monomers can be used in combination in the present invention.

Examples of the other crosslinkable components include a wide variety of compounds each containing two or more functional groups. Illustrative are triallyl cyanurate, triallyl isocyanurate, triallyl phosphate, triallylamine, poly(meth)alkyloxyalkanes, (poly)ethylene glycol diglycidyl ether, glycerol diglycidyl ether, ethylene glycol, polyethylene glycol, propylene glycol, glycerin, pentaerythritol, ethylenediamine, polyethyleneimine, glycidyl(meth)acrylate, triallyl isocyanurate, trimethylol propane di(meth)allyl ether, tetraallyloxyethane, and glycerol propoxytriacrylate, although they differ depending on the substituent groups in the fluorescence sensor substance to be used. Two or more of these crosslinkable monomers can be used in combination in the present invention.

Examples of the cationic monomers cable of providing cations in water include dimethylaminoethyl(meth)acrylate, diethylaminoethyl(meth)acrylate, and 4-vinylpyridine. Two or more of these cationic monomers can be used in combination in the present invention.

Examples of the anionic monomers capable of providing anions in water include (meth)acrylic acid, vinylpropionic acid, and 4-vinylbenzenesulfonic acid. Two or more of these anionic monomers can be used in combination in the present invention.

Examples of the nonionic monomers containing no groups capable of liberating ions in water include 2-hydroxyethyl (meth)acrylate, 3-methoxypropyl (meth)acrylate, 4-hydroxydibutyl(meth)acrylate, 2-methoxyethyl acrylate, and 1,4-cyclohexanedimethanol monoacrylate. Two or more of these nonionic monomers can be used in combination in the present invention.

Further, two or more of these crosslinkable monomers, other crosslinkable components, cationic monomers, anionic monomers and nonionic monomers can also be used in combination. The proportion of one or more of these other components can be preferably from 0.1 to 10 mole %, more preferably from 2 to 7 mole % based on the total proportion of the fluorescent monomer compound and the polymerizable monomer with the (meth)acrylamide residual group contained therein. The combined use of one or more of these other components makes it possible to form a three-dimensional crosslinked structure, and also to effect an adjustment of hydrophilicity, the introduction of starting points for a reaction, and the like. Concerning three-dimensional crosslinked structures, a description will be made subsequently herein.

The fluorescence sensor substance according to the present invention can preferably have a structure represented by the following formula (7):

Formula (7)

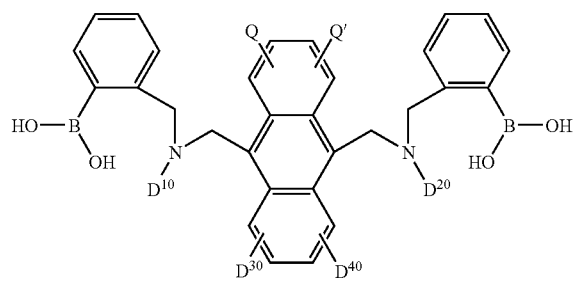

In the formula (7), Q and Q' are as defined in connection with the fluorescent monomer compound represented by the formula (1). $D^{10}$, $D^{20}$, $D^{30}$ and $D^{40}$ have meanings of the following definition (x) or (xx):

(x) $D^{10}$ and $D^{20}$ may be the same or different and are each a substituted or unsubstituted alkyl group, $D^{30}$ is a hydrogen atom, and $D^{40}$ is a substituent group represented by the below-described formula (8). As the alkyl group, methyl, ethyl, propyl, butyl, pentyl or the like is preferred, with methyl or ethyl being more preferred.

(xx) $D^{10}$ and $D^{20}$ may be the same or different and are each a substituent group represented by the below-described formula (9), and $D^{30}$ and $D^{40}$ may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups. As the alkyl group, one having 1 to 10 carbon atoms is preferred. Specific examples include methyl, ethyl, propyl, butyl, and pentyl. Examples of the acyl group include formyl, acetyl, propionyl, butyryl, and isobutyryl. Examples of the oxyalkyl group include methoxy and ethoxy. Examples of the halogen atoms include F, Cl, Br, and I. Examples of the aminoalkyl group include methylamino and ethylamino.

Introduction of nitro, cyano and/or acyl groups as Q, Q', $D^{30}$ and $D^{40}$ can bring about an effect that contributes to the red-shift of fluorescence or the widening of the distance between an excitation wavelength peak and a fluorescence wavelength peak.

When $D^{10}$, $D^{20}$, $D^{30}$ and $D^{40}$ have the meanings of the definition (xx) in the present invention, it is preferred that at least one of Q, Q', $D^{30}$ and $D^{40}$ is a substituent group selected from acetyl, carboxylate ester and cyano groups and the remainder(s) is(are) hydrogen atom(s).

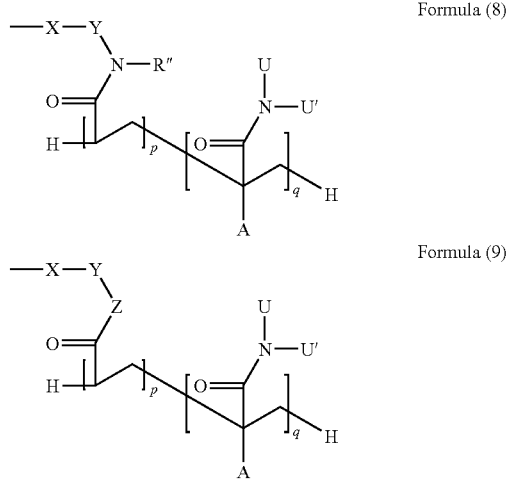

Formula (8)

Formula (9)

A description will first be made of a case in which D10, D20, D30 and D40 have the meanings of the definition (x) in the formula (8).

In the definition (x), X is a substituent group selected from the group consisting of —COO—, —OCO—, —CH$_2$NR—, —CH$_2$S—, —CH$_2$O—, —NR—, —NRCO—, —CONR—, —SO$_2$NR—, —NRSO$_2$—, —O—, —S—, —SS—, —NRCOO—, —OCONR— and —CO—. Examples of the alkyl group include methyl, ethyl, propyl, butyl and pentyl. Preferred examples of X include —NRCO— and —CONR—.

In the definition (x), Y and R" are as defined in connection with the fluorescent monomer compound represented by the formula (1), and U, U' and A are as defined in connection with the polymerizable monomer containing the (meth)acrylamide residual group, which is represented by the formula (6).

In the definition (x), the molar ratio (p:q) of p to q in the formula (8) can be preferably from 1:10 to 1:4,000, more preferably from 1:50 to 1:4,000, particularly preferably from 1:100 to 1:2,000. A value of p greater than that giving the molar ratio of 1:10 involves a potential problem that the degree of freedom may be lost due to the bulkiness of the hydrophobic moieties and the interaction with a saccharide may be reduced. A value of p smaller than that giving the molar ratio of 1:4,000, on the other hand, may not be able to assure the absolutely-needed level of fluorescence intensity.

A description will next be made of a case in which $D^{10}$, $D^{20}$, $D^{30}$ and $D^{40}$ have the meanings of the definition (xx) in the formula (7).

In the definition (xx), X represents a C1-C30 alkylene group containing at least one substituent group selected from the group consisting of —COO—, —OCO—, —CH$_2$NR—, —NR—, —NRCO—, —CONR—, —SO$_2$NR—, —NRSO$_2$—, —O—, —S—, —SS—, —NRCOO—, —OCONR— and —CO—. R represents a hydrogen atom or a substituted or unsubstituted alkyl group. The expression "alkylene group containing at least one substituent group" as used herein means an alkylene group containing at least one substituent group at an end thereof or an alkylene group containing at least one substituent group in the chain thereof. The carbon number of the alkylene group may be preferably from 1 to 30, more preferably from 3 to 12. Specific examples include propylene, hexylene and octylene. As the at least one substituent group contained in the alkylene group, —NRCO— or —CONR— is preferred. When R is an alkyl group, one having 1 to 10 carbon atoms being preferred, with 1 to 5 being more preferred. Specific examples include methyl, ethyl, propyl, butyl and pentyl. As R, a hydrogen atom is preferred.

In the definition (xx), Y and Z are as defined in connection with the fluorescent monomer compound represented by the formula (1), and U, U' and A are as defined in connection with the polymerizable monomer containing the (meth)acrylamide residual group, which is represented by the formula (5).

In the definition (xx), the molar ratio (p:q) of p to q in the formula (7) can be preferably from 1:50 to 1:6,000, more preferably from 1:150 to 1:3,000. A value of p greater than that giving the molar ratio of 1:50 involves a potential problem that the degree of freedom may be lost due to the bulkiness of the hydrophobic moieties and the interaction with a saccharide may be reduced. A value of p smaller than that giving the molar ratio of 1:6,000, on the other hand, may not be able to assure the absolutely-needed level of fluorescence intensity.

In the fluorescence sensor substance useful in the present invention, at least a portion of the copolymer may form intermolecular crosslinks to present a three-dimensional crosslinked structure. The formation of three-dimensional crosslinks across poly(meth)acrylamide chains is preferred because the fluorescent monomer compound becomes resistant to flowing out. It is to be noted that, although the fluorescent monomer compound according to the present invention contains hydrophobic moieties capable of emitting fluorescence upon binding a saccharide as described above, the hydrophobic moieties are assured to retain such a degree of freedom as permitting the binding of the saccharide in an aqueous solution because the hydrophobic moieties are bonded to poly(meth)acrylamide chains via their divalent, organic residual groups represented by Y. The detection sensitivity for the saccharide is, therefore, not lowered despite the formation of the three-dimensional crosslinked structure.

Although no particular limitations are imposed on the production processes of the fluorescent monomer compound and fluorescence sensor substance according to the present invention and the method of formation of the three-dimensional crosslinked structure, they can be produced by the following processes.

(1-1) Production Process of a Fluorescent Monomer Compound

In accordance with a synthesis scheme shown in FIG. 1, a description will be made about one example of a process for the production of a compound of the formula (1) in which Q and Q' are each a hydrogen atom, $D^1$ and $D^2$ are each a methyl group, $D^3$ is a hydrogen, $D^4$ is a substituent group represented by the formula (2), X is —CONH, Y is —$C_6H_{12}$— and R" is a hydrogen atom (9,10-bis[[N-methyl-N-(ortho-boronobenzyl)amino]methyl]anthracene-2-carboxylic acid-1-(6-acrylamido-n-hexyl)amide).

Using methyl-9,10-dimethylanthracene-2-carboxylic acid as a raw material, N-bromosuccinimide (NBS) is reacted with it to yield methyl 9,10-bis(bromomethyl)anthracene-2-carboxylate. Subsequent addition of methylamine converts the bromomethyl group into an aminomethyl group. 2-(2-Bromomethylphenyl)-1,3-dioxaborinane is reacted with the resultant methyl 9,10-bis(aminomethyl)anthracene-2-carboxylate to obtain methyl 9,10-bis[[N-methyl-N-(ortho-boronobenzyl)amino]methyl]anthracene-2-carboxylate. On the reaction product, an alkali is then caused to act to induce de-esterification, whereby 9,10-bis[[N-methyl-N-(ortho-boronobenzyl)amino]methyl]anthracene-2-carboxylic acid is obtained. Bonding of 1-acrylamido-6-aminohexane to the carboxylic acid can afford the target compound.

Described more specifically, a solution of methyl-9,10-dimethylanthracene-2-carboxylic acid is prepared preferably at a concentration of from 1 to 20 g/L, with 10 to 15 g/L being more preferred. NBS is added to the solution such that the molar ratio of NBS to methyl-9,10-dimethylanthracene-2-carboxylic acid ranges preferably from 2 to 2.5 times, more preferably from 2.1 to 2.2 times. In each of the above-described synthesis reactions for the target compound, it is possible to use a solvent suited for the corresponding reaction product. Examples of such a solvent include chloroform, carbon tetrachloride, n-hexane, acetonitrile, dimethylformamide, and dimethylsulfoxide. These solvents can be used either singly or in combination. To dissolve methyl-9,10-dimethylanthracene-2-carboxylic acid, for example, chloroform, carbon tetrachloride, acetonitrile or the like can be suitably used. Two or more of these solvents may be used in combination, that is, as a mixed solution. Upon using two or more of these solvents in combination, the proportions of such two or more solvents can be set as desired. The reaction temperature is preferably from 60 to 120° C., more preferably from 80 to 100° C., and the reaction time is preferably from 0.5 to 6 hours, more preferably from 2 to 4 hours.

With methyl 9,10-bis(bromomethyl)anthracene-2-carboxylate which has been dissolved preferably at a concentration of from 1 to 30 g/L, more preferably at a concentration of from 2 to 10 g/L in a solvent, methylamine is next mixed in a proportion of preferably from 2 to 30 molar times, more preferably from 6 to 20 molar times to react them with each other. The reaction temperature is preferably from 0 to 60° C., more preferably from 20 to 30° C., and the reaction time is preferably from 1 to 10 hours, more preferably from 2 to 5 hours.

The reaction between the thus-obtained methyl 9,10-bis(aminomethyl)anthracene-2-carboxylate and 2-(2-bromomethylphenyl)-1,3-dioxaborinane is conducted by mixing them together such that the proportion of 2-(2-bromomethylphenyl)-1,3-dioxaborinane becomes preferably 2 to 8 times, more preferably 3 to 5 times relative to methyl 9,10-bis(aminomethyl)anthracene-2-carboxylate. The concentration of methyl 9,10-bis(aminomethyl)anthracene-2-carboxylate is preferably from 10 to 200 g/L, more preferably from 50 to 100 g/L. The reaction temperature is preferably from 0 to 80° C., more preferably from 20 to 40° C., and the reaction time is preferably from 1 to 48 hours, more preferably from 2 to 24 hours.

Methyl 9,10-bis[[N-methyl-N-(ortho-boronobenzyl)amino]methyl]anthracene-2-carboxylate is next hydrolyzed with an alkali. As the alkali, any alkaline agent can be used such as sodium hydroxide or potassium hydroxide. The reaction temperature is preferably from 0 to 100° C., more preferably from 20 to 60° C., and the reaction time is preferably from 1 to 24 hours, more preferably from 2 to 6 hours.

With 9,10-bis[[N-methyl-N-(ortho-boronobenzyl)amino]methyl]anthracene-2-carboxylic acid (1 mole), 1-acrylamido-6-aminohexane (preferably 1.05 to 3.0 moles, more preferably 1.2 to 1.4 moles) and a condensing agent (preferably 1.0 to 3.0 moles, more preferably 1.1 to 2.0 moles) are then mixed. As the condensing agent, dicyclohexylcarbodiimide, 1-[3-(dimethylamino)propyl]-3-ethylcarbodiimide or the like can be used. The reaction temperature is preferably from 0 to 60° C., more preferably from 20 to 30° C., and the reaction time is preferably from 1 to 24 hours, more preferably from 2 to 15 hours.

It is to be noted that, when a raw compound having, as the substituents represented by Q and Q' in the formula (1), groups different from the corresponding groups in the above-described compound is used as the anthracene skeleton, a corresponding compound can be produced by making suitable selections as to the solvent, additives, reaction temperature, reaction time, isolation method, etc. Further, use of a compound with a sulfonyl group contained on an anthracene skeleton in place of methyl carboxylate makes it possible to introduce $SO_2NH$— as X. Furthermore, addition of amino-$(C_2H_4O)$m-acrylamide in place of 1-acrylamido-6-aminohexane makes it possible to introduce —$(C_2H_4O)$m- as Y.

It is also to be noted that 9,10-bis[[N-methyl-N-(ortho-borobenzyl)amino]methyl]anthracene-2-carboxylic acid can also be prepared by using anthryldiamine-2-carboxylic acid in place of anthryldiamine in Example 3 of Japanese Patent laid-open No. Hei 8-53467.

(1-2) Production Process of Another Fluorescent Monomer Compound

Figure 2:
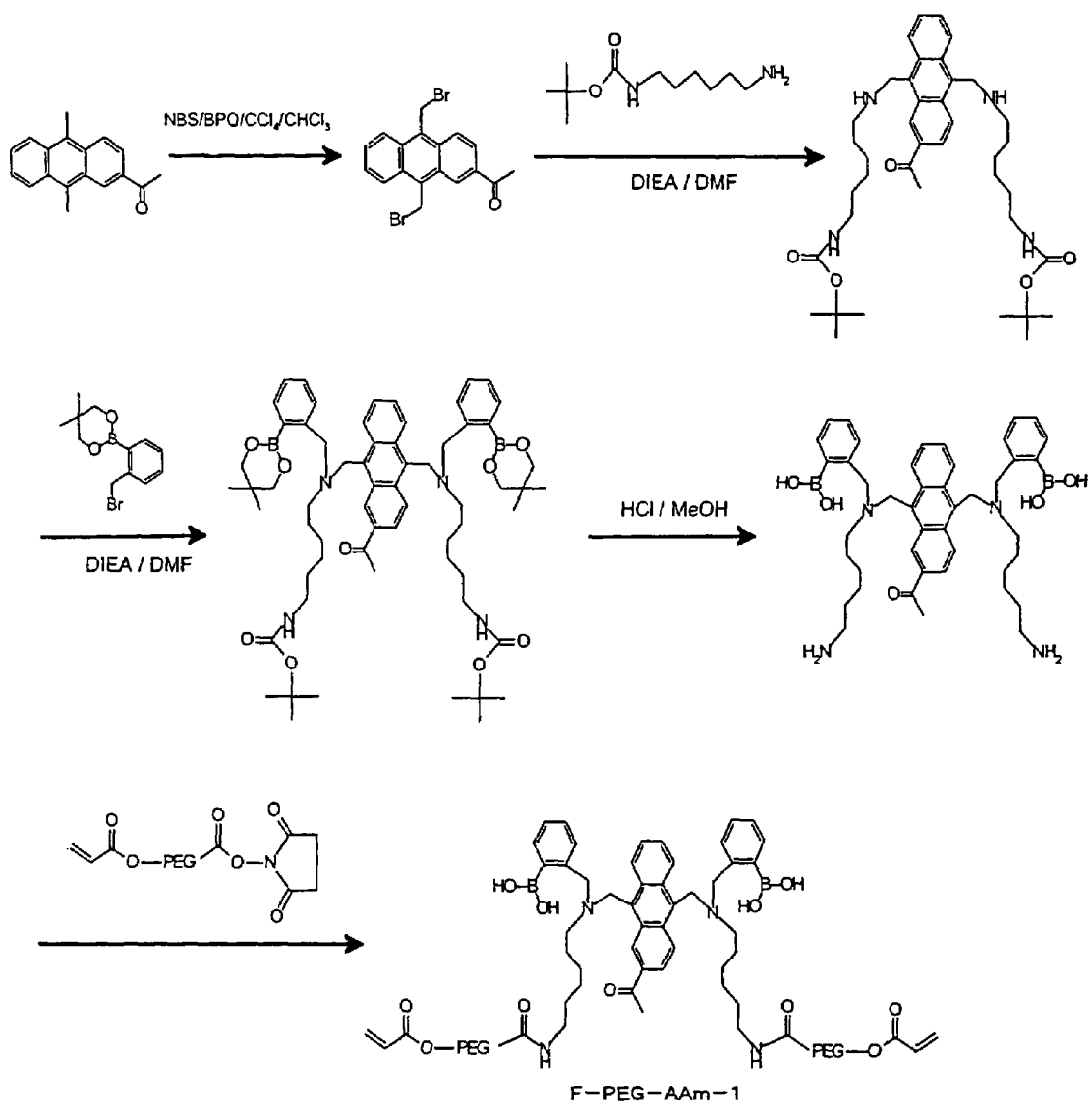
FIG. 2 is a diagram showing one example of a synthesis scheme for 9,10-bis(methylene)[[N-(ortho-boronobenzyl)methylene]-N-[(acryloylpolyoxyethylene)carbonylamino]-n-hexamethylene]-2-acetylanthracene (F-PEG-AAm-1).

In accordance with a synthesis scheme shown in FIG. 2, a description will be made about one example of a process for the production of a compound of the formula (1) in which Q, Q' and $D^3$ are each a hydrogen atom, $D^4$ is —$COCH_3$, $D^1$ and $D^2$ are each a substituent group represented by the formula (3), $D^1$ and $D^2$ are the same, X is —$C_6H_{12}$—NHCO—, Y is a PEG residual group, and Z is —O— {9,10-bis(methylene)[[N-ortho-boronobenzyl) methylene]-N-[(acryloylpolyoxyethylene)carbonylamino]-n-hexamethylene]-2-acetylanthracene (F-PEG-AAm-1)}.

Using 2-acetyl-9,10-dimethylanthracene as a raw material, it is heated in a carbon tetrachloride/chloroform solvent, and is reacted with N-bromosuccinimide (NBS) and benzoyl peroxide (BPO) to afford 2-acetyl-9,10-bis(bromomethylene)anthracene. It is then reacted with N-(t-butoxycarbonyl)-hexyldiamine in the presence of a base such as diisopropylethylamine (DIEA) in a solvent such as dimethylformamide (DMF). As a result, the bromomethylene group is converted into a [(t-butoxycarbonylamino)hexylamino]

methylene group. 2-(2-Bromomethylphenyl)-1,3-dioxaborinane is caused to act on the reaction product in the presence of a base such as DIEA in a solvent such as DMF to yield 9,10-bis[[N-6'-(t-butoxycarbonylamino)hexyl-N-[2-(5,5-dimethylborinane-2-yl)benzyl]amino]methylene]2-acetylanthracene. An acid such as hydrochloric acid is caused to act on the reaction product for its deprotection to obtain 9,10-bis(methylene)[[N-(ortho-boronobenzyl)methylene]-N-(aminohexyl)]-2-acetylanthracene. It is then reacted with acryloyl-(polyethylene glycol)-N-hydroxysuccinimide ester to obtain the target compound.

It is to be noted that, when a raw compound having, as the substituent represented by $D^4$ in the formula (1), a group different from the corresponding group in the above-described compound is used as the anthracene skeleton, a corresponding compound with a group other than an acetyl group contained as $D^4$ can be produced by making suitable selections as to the solvent, additives, reaction temperature, reaction time, isolation method, etc.

(1-3) Production Process of a Further Fluorescent Monomer Compound

Figure 3:
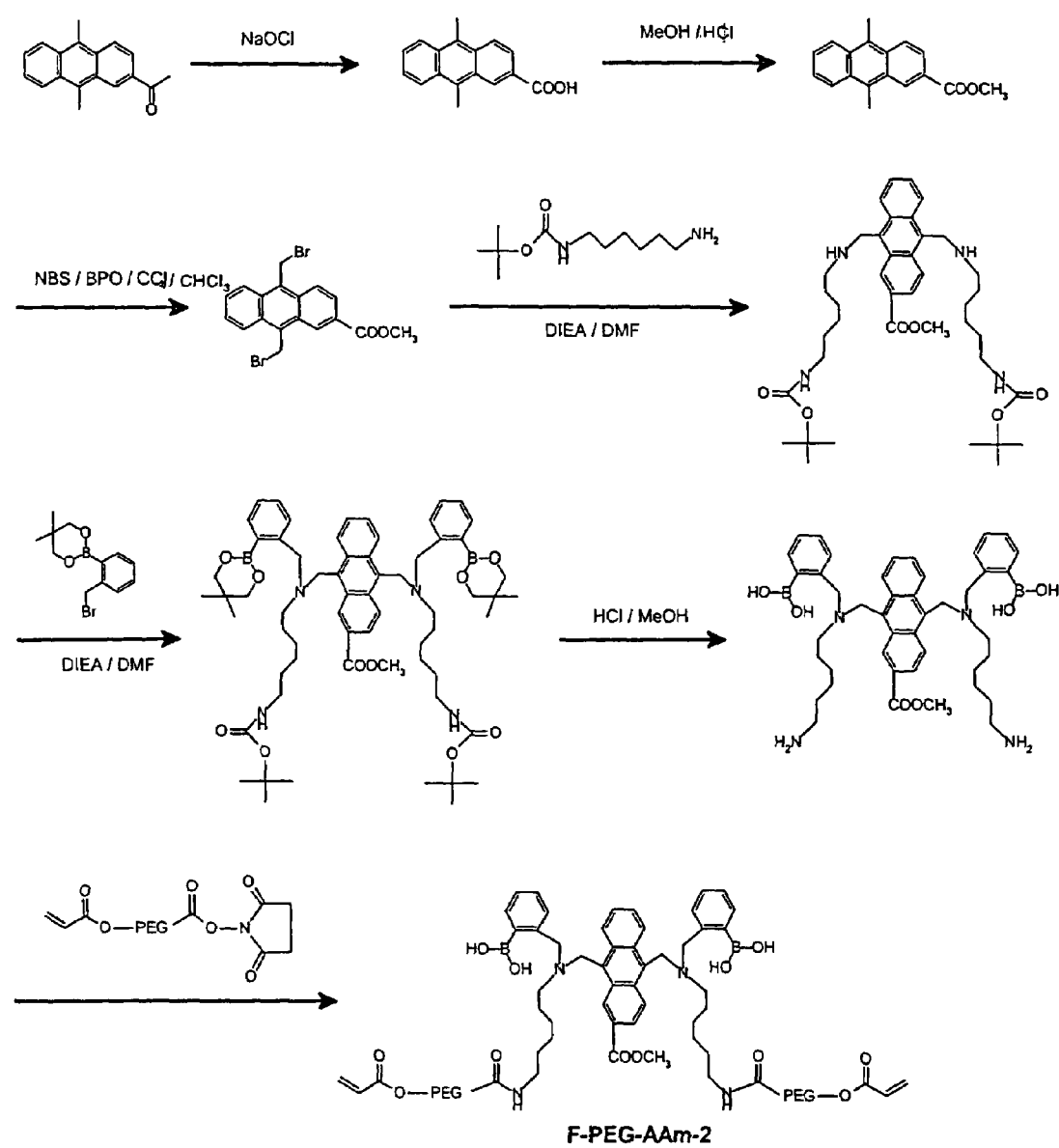
FIG. 3 is a diagram showing one example of a synthesis scheme for methyl 9,10-bis(methylene)[[N-(ortho-boronobenzyl)methylene]-N-[(acryloylpolyoxyethylene)carbonylamino]-n-hexamethylene]anthracene-2-carboxylate (F-PEG-AAm-2).

In accordance with a synthesis scheme shown in FIG. 3, a description will be made about one example of a process for the production of a compound of the formula (1) in which Q, Q' and D3 are each a hydrogen atom, $D^4$ is —COOCH$_3$, $D^1$ and $D^2$ are each a substituent group represented by the formula (3), $D^1$ and $D^2$ are the same, X is —C$_6$H$_{12}$—NHCO—, Y is a PEG residual group, and Z is —O— {methyl 9,10-bis(methylene)[[N-ortho-boronobenzyl)methylene]-N-[(acryloylpolyoxyethylene)carbonylamino]-n-hexamethylene]anthracene-2-carboxylate (F-PEG-AAm-2)}.

Using 9,10-dimethyl-2-acetylanthracene as a raw material, it is added to dioxane/aqueous solution of sodium perchlorate. Subsequent to stirring under heat, an acid is added to obtain a precipitate of 9,10-dimethylacetone-2-carboxylic acid. The precipitate is then dissolved in hydrochloric acid/methanol solvent, and the resulting solution is heated under reflux to afford methyl 9,10-dimethylanthracene-2-carboxylate. The methyl ester is dissolved in carbon a tetrachloride/chloroform solvent. Subsequent to heating, the methyl ester is reacted with N-bromosuccinimide (NBS) and benzoyl peroxide (BPO) to convert the methyl ester into methyl 9,10-bis(bromomethylene)anthracene-2-carboxylate. The thus-obtained methyl ester is then reacted with N-(t-butoxycarbonyl)-hexyldiamine in the presence of a base such as diisopropylethylamine (DIEA) in a solvent such as dimethylformamide (DMF). As a result, the bromomethylene group is converted into a [(t-butoxycarbonylamino)hexylamino]methylene group. 2-(2-Bromomethylphenyl)-1,3-dioxaborinane is caused to act on the reaction product in the presence of a base such as DIEA in a solvent such as DMF to yield methyl 9,10-bis[[N-6'-(t-butoxycarbonylamino)hexyl-N-[2-(5,5-dimethylborinan-2-yl)benzyl]amino]methyl]anthracene-2-carboxylate. When deprotected under the action of an acid such as hydrochloric acid, it provides methyl 9,10-bis(methylene)[[N-(orthoboronobenzyl)methylene]-N-(aminohexyl)]anthracene-2-carboxylate. It is then reacted with acryloyl-(polyethylene glycol)-N-hydroxysuccinimide ester in a basic buffer to afford the target compound.

It is to be noted that, when a raw compound having, as the substituent represented by $D^4$ in the formula (1), a group different from the corresponding groups in the above-described compounds is used as the anthracene skeleton, a corresponding compound with a group other than a methyl carboxylate group contained as $D^4$ can be produced by making suitable selections as to the solvent, additives, reaction temperature, reaction time, isolation method, etc.

(2) Production Process of a Fluorescence Sensor Substance

The copolymerization between the fluorescent monomer compound represented by the formula (1) and the polymerizable monomer containing the (meth)acrylamide residual group can be conducted using a polymerization accelerator or polymerization initiator in a solvent. When $D^1$, $D^2$, $D^3$ and $D^4$ have meanings of the definition (i) in the chemical formula (1), a solvent may preferably be composed of one or more solvents selected from the group consisting of dimethyl sulfoxide, dimethyl formamide, ethylene glycol and diethylene glycol solvent. The solvent may be used as a mixture with water. In particular, use of a mixed solution composed of dimethyl sulfoxide or dimethyl formamide and water can promote the progress of polymerization. When mixed with water, it is preferred to use one containing dimethyl sulfoxide and/or dimethyl formamide at a concentration of from 40 to 80 wt %, with 50 to 70 wt % being more preferred. In this concentration range, the mixed solution can promote the progress of polymerization and can obtain the target fluorescence sensor substance with a high yield. It is to be noted that a solvent concentration lower than 40 wt % may result in the initiation of precipitation of the fluorescent monomer compound before the initiation of polymerization. When $D^1$, $D^2$, $D^3$ and $D^4$ have meanings of the definition (ii) in the chemical formula (1), water may be used as a solvent. The introduction of Y, which has hydrophilicity of such an extent as permitting providing the fluorescent monomer compound with solubility in water, has made it possible to conduct polymerization even when water alone is used as a solvent. It is also possible to use water in the form of a mixture with one or more of dimethyl sulfoxide, dimethyl formamide, ethylene glycol, diethylene glycol and the like. When an organic solvent is mixed in the present invention, its content is preferably from 10 to 50 wt %, more preferably from 20 to 30 wt %.

Upon copolymerizing the fluorescent monomer compound represented by the formula (1) and the polymerizable monomer containing the (meth)acrylamide residual group, one or more other components may be added. When one or more other components are added, its or their proportion is preferably from 0.1 to 10 mole %, more preferably from 2 to 7 mole % based on the total proportion of the fluorescent monomer compound and the polymerizable monomer containing the (meth)acrylamide residual group. When one or more other components are added, it is preferred to concurrently add a polymerization initiator and polymerization promoter upon conducting polymerization.

Examples of the polymerization initiator include persulfates such as sodium persulfate, potassium persulfate and ammonium persulfate; hydrogen peroxide; azo compounds such as azobis-2-methylpropionamidine hydrochloride and azoisobutyronitrile; and peroxides such as benzoyl peroxide, lauroyl peroxide, cumene hydroperoxide and benzoyl peroxide. These polymerization initiators can be used either singly or in combination. In combination with such a polymerization initiator, it is also possible to use, as a polymerization promoter, one or more of reducing agents such as sodium hydrogensulfite, sodium sulfate, Mohr's salt, sodium pyrobisulfite, sodium formaldehydesulfoxylate, and ascorbic acid; and amine compounds such as ethylenediamine, sodium ethylenediaminetetraacetate, glycine, and N,N,N',N'-tetramethylethylenediamine. The polymerization temperature is preferably from 15 to 75° C., more preferably from 20 to 60° C., while the polymerization time is preferably from 1 to 20 hours, more preferably from 2 to 8 hours. Combined use of a persulfate as a polymerization initiator with N,N,N',N'-tetramethylethylenediamine as a polymerization promoter is particularly preferred in that the polymerization can be conducted at room temperature.

The compound represented by the formula (7), on the other hand, can also be produced without relying upon the copolymerization of the fluorescent monomer compound represented by the formula (1) with the polymerizable monomer containing the (meth)acrylamide residual group. As the fluorescent monomer compound represented by the formula (1) is synthesized through plural steps, the fluorescence sensor substance represented by the formula (7) can also be eventually produced even when instead of using the fluorescent monomer compound represented by the formula (1) as a raw material, another compound is caused to act on an intermediate product for the fluorescent monomer compound. For example, the fluorescence sensor substance represented by the formula (7) can also be produced even when 9,10-bis[[N-(6'-aminohexyl)-N-(ortho-boronobenzyl)amino]methyl]-2-acetylanthracene shown in the scheme of FIG. 2 or methyl 9,10-bis[[N-(6'-aminohexyl)-N-(ortho-boronobenzyl) amino]methyl]anthracene-2-carboxylate shown in the scheme of FIG. 3 and one obtained by introducing carboxyl groups into a polymer of the polymerizable monomer, which contains the (meth)acrylamide residual group, are reacted in the presence of a coupling reagent. As another example, the fluorescence sensor substance represented by the formula (7) can also be produced when subsequent to the advance polymerization of the polymerizable monomer containing the (meth)acrylamide residual group, the resulting polymer is copolymerized with the fluorescent monomer compound in the presence of a polymerization initiator and polymerization promoter.

(3) Method of Formation of a Three-dimensional Crosslinked Structure

It is preferred that at least a portion of the fluorescence sensor substance according to the present invention forms intermolecular crosslinks and has a three-dimensional crosslinked structure. As mentioned above, the formation of the three-dimensional crosslinked structure across poly (meth)acrylamide chains makes the fluorescent monomer compound resistant to flowing out, and therefore, makes it possible to detect a saccharide with ease.

No limitation is imposed on the method for the introduction of such a three-dimensional crosslinked structure. For example, intermolecular crosslinks can be formed between at least some molecules of the fluorescence sensor substance by causing a crosslinking component to act on the fluorescence sensor substance.

As an alternative, such a three-dimensional crosslinked structure can also be formed by copolymerizing the fluorescent monomer compound represented by the formula (1) and the polymerizable monomer containing the (meth)acrylamide residual group as described above.

Upon using the fluorescence sensor substance as an implantable, saccharide-measuring sensor, the fluorescence sensor substance is generally on a support material to prevent it from flowing out. The immobilization on the support material and the formation of three-dimensional crosslinks can be effected at the same time by using, as such a support material, the polymerizable monomer containing the (meth)acrylamide residual group or its polymer and polymerizing it with the fluorescent monomer compound represented by the formula (1) while using a crosslinking component as needed.

Usable examples of the crosslinking component include the crosslinkable monomers, other crosslinkable components, cationic monomers, anionic monomers and nonionic monomers described above as other components which can be added to the fluorescence sensor substance. The crosslinkable monomers and other crosslinkable components can be used more preferably. These crosslinking components can be used either singly or in combination in the present invention.

In the third aspect of the present invention, there is also provided a detector layer with the above-described fluorescence sensor substance immobilized on a support material. In the fourth aspect of the present invention, there is also provided an implantable, saccharide-measuring sensor comprising the above-described fluorescence sensor substance or detector layer.

Figure 4:
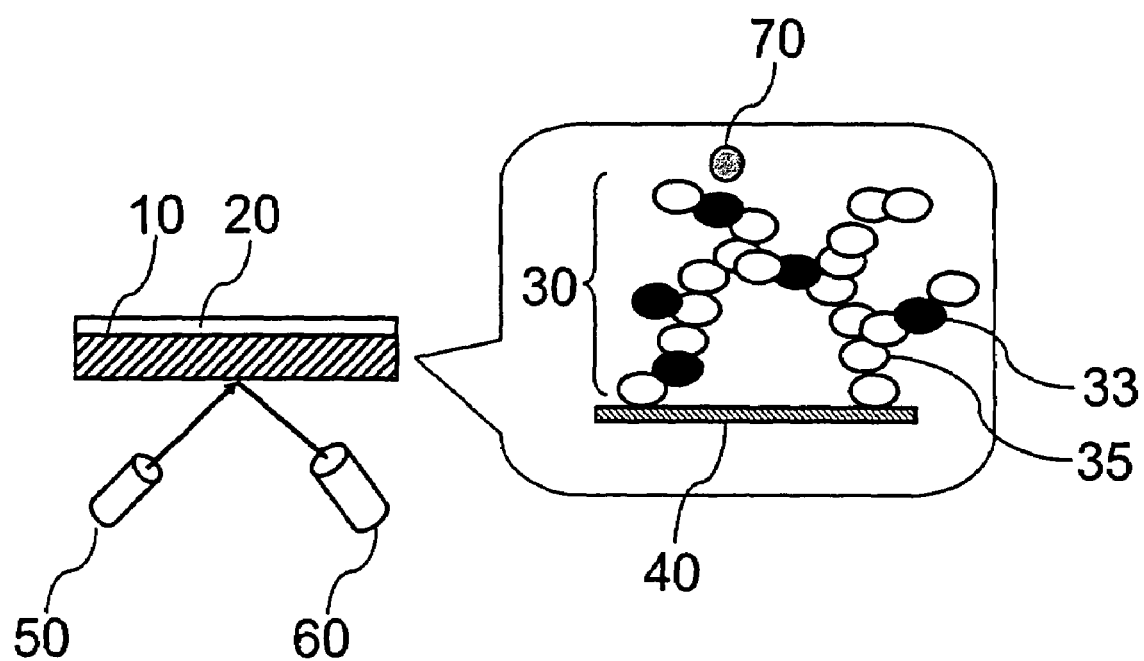
FIG. 4 is a schematic diagram showing one example of a detector layer with a fluorescence sensor substance according to the present invention immobilized on a support material.

The implantable, saccharide-measuring sensor may preferably be immobilized via covalent bonds or hydrophobic bonds or by electrical or other interactions on an immobilizing material such as a support material such that the fluorescence sensor substance is prevented from flowing out. An outline of a saccharide detection method making use of the fluorescence sensor substance according to the present invention will be described with reference to FIG. 4. FIG. 4 is a schematic view illustrating one example of a detector layer with the fluorescence sensor substance according to the present invention immobilized on a support material.

The sensor includes a detector layer 10, in which a fluorescence sensor substance 30 is immobilized on a support material 40. The fluorescence sensor substance 30 is a copolymer, which at least includes fluorescent monomer compound moieties 33 indicated by oval dots and polymerizable monomer moieties 35 having a (meth)acrylamide residual group and indicated by oval circles. Fluorescence is emitted when a saccharide 70 in an aqueous solution interacts with the fluorescent monomer compound 33. The detector layer 10 may have an optical isolation layer 20. Light of 350 to 420 nm in wavelength is irradiated from a light source 50 onto the detector layer 10, and a change in reflected fluorescence intensity or wavelength is detected by a detector 60. As a result, the concentration of the saccharide can be determined relying upon the fluorescence intensity. Examples of the support material employed in the detector layer according to the present invention include a wide variety of materials, for examples, inorganic materials such as glass and metals and organic materials such as plastic films. Preferred as the support material for the detector layer for use in the saccharide-measuring sensor is a material that is excellent in transparency and does not dissolve or flow out even in body fluids. Among glass and plastic films, poly(meth)acrylamide films and poly(meth)acrylate films can be preferably used in the present invention. The use of a poly(meth)acrylamide as a support material is advantageous in that the immobilization of the fluorescence sensor substance on the support material and the formation of three-dimensional crosslinked structure can be effected at the same time as mentioned above. Crosslinked structures available from the use of a crosslinkable polymer are formed, as illustrated in FIG. 4, between polymerizable monomer moieties 35, which contain (meth)acrylamide residual groups, themselves, between fluorescent monomer moieties 33 and polymerizable monomer moieties 35 containing (meth)acrylamide residual groups, and between polymerizable monomer moieties 35 containing (meth)acrylamide residual groups and the support material 40.

Upon immobilizing the fluorescence sensor substance on a surface of a support material made of an inorganic material or organic material, the support material and the fluorescence sensor substance can be chemically bonded together with a crosslinking agent or the like. Examples of such a crosslinking agent include silane coupling agents represented by the following formula (10):

(R'''O)3-Si-E                                   Formula (10)

In the formula (10), R'''O represents a C1-C5 alkoxy group such as methoxy, ethoxy or propoxy, with methoxy or ethoxy being preferred. An inorganic material can be chemically bonded with such alkoxy groups. E is a functional group capable of being chemically bonded with an organic material, such as vinyl, epoxy, amino, mercapto, acryl, methacryl, (meth)acryloyl, or a derivative thereof. Illustrative silane coupling agents suitable for use in the present invention include vinylmethoxysilane, 3-glycidoxypropyltrimethoxysilane, N-2-(aminoethyl)-3-aminopropylethoxysilaine, 3-mercaptopropyltrimethoxysilane, 3-acryloxypropyltrimethoxysilane, 3-methacryloxypropyltrimethoxysilane, and 3-methacryloxypropyltriethoxysilane.

Among the above-described silane coupling agents, those containing as E a substituent group that contains a polymerizable double bond, such as acryl, methacryl or (meth)acryloyl, are also suited for the reasons to be mentioned below. If such a silane coupling agent is applied beforehand on the surface of an inorganic material such as glass or metal, the fluorescent monomer compound, which contains phenylboronic acid residual groups and acrylamide residual groups, and the polymerizable monomer, which contains (meth)acrylamide residual group, can be directly immobilized while copolymerizing them together.

To immobilize the fluorescence sensor substance on a surface of an organic material such as a plastic film, on the other hand, substituent groups containing reactive groups can be introduced into the plastic film to bond them with the fluorescence sensor substance. As a process for introducing such reactive groups, there is, for example, a graft polymerization process of glycidyl(meth)acrylate by plasmas, electron rays, radiations or the like as disclosed in Japanese Patent raid-open No. Hei 5-245198.

To further facilitate the bonding of the fluorescence sensor substance to an inorganic material or organic material treated with such a silane coupling agent or to a plastic film in which reactive groups have been introduced, a monomer with one or more reactive substituent groups contained therein may be used beforehand upon synthesis of the fluorescence sensor substance, or subsequent to the synthesis of the fluorescence sensor substance, reactive groups may be introduced. As such a monomer, those described above in connection with the florescence sensor substance are each usable. Examples of such reactive groups include amino, carboxyl, hydroxyl, halogenated carboxyl, sulfonyl, thiol, isocyanate, isothiocyanate, and epoxy groups. It is to be noted that the bonding between the reactive groups and the fluorescence sensor substance on the inorganic or organic material treated with the silane coupling agent can be effected in the presence or absence of suitable solvent, catalyst and condensing agent.

It is preferred to include a fluorescence detector in the implantable, saccharide-measuring sensor according to the present invention. More desirably, such sensor and fluorescence detector can be arranged together with a light source within an adequate housing.

Upon using the fluorescence sensor substance and detector layer according to the present invention in the implantable, saccharide-measuring sensor, it is preferred to laminate the optical isolation layer 20 on the detector layer 10 as illustrated in FIG. 4. When the optical isolation layer 20 is arranged on the side of an outer surface of the sensor, the optical isolation layer 20 can avoid any contact of the fluorescence sensor substance, which is contained in the detector layer 10, with radicals, oxidizing substances, reducing substances and the like as components of a body fluid, and can protect the fluorescence sensor substance from deteriorations by such body fluid components. Further, the lamination of the optical isolation layer 20 makes it possible to avoid a reduction in detection ability which would otherwise take place due to reflection and scattering of excitation light emitted from the light source 50. Furthermore, even when a biosubstance other than the saccharide is excited by excitation light from the light source, the arrangement of the optical isolation layer 20 can shield any light originated from the outside other than the excitation light from the light source 50, and can also eliminate effects of any color substances or fluorescent substances in the body.

The optical isolation layer 20 provided with such functions as described above is formed of a support material for the optical isolation layer and an opaque material. As the support material for the optical isolation layer, it is possible to choose a macromolecular material which may be crosslinked or chemically modified. Examples of the macromolecular material include dextran, poly(meth)acrylamides, poly(meth)acrylates, polyethylene glycol, polyvinyl alcohol, polyamides, polyurethanes, their mixtures, and their copolymers. The support material for the optical isolation layer may be modified with vitamin E, a polyphenol, a metal chelate or the like, or may carry such a compound thereon. Usable examples of the opaque material include carbon black, fullerene, carbon nanotubes, and iron oxide.

The detector layer 10 and the optical isolation layer 20 can be laminated together via chemical bonds such as covalent bonds, ionic bonds or hydrophobic bonds. When the optical isolation layer uses dextran as its support material and carbon black as its opaque material, for example, dextran is dissolved in a solvent, followed by the addition of carbon black. The resulting mixture is rendered uniform by ultrasonication, to which an aqueous solution of an alkali and ethylene glycol diglycidyl ether are added further. The thus-prepared solution is then evenly sprayed by a sprayer onto the detector layer, and the detector layer with the solution sprayed thereon is then heated and dried to laminate an optical isolation layer on the detector layer.

Figure 5:
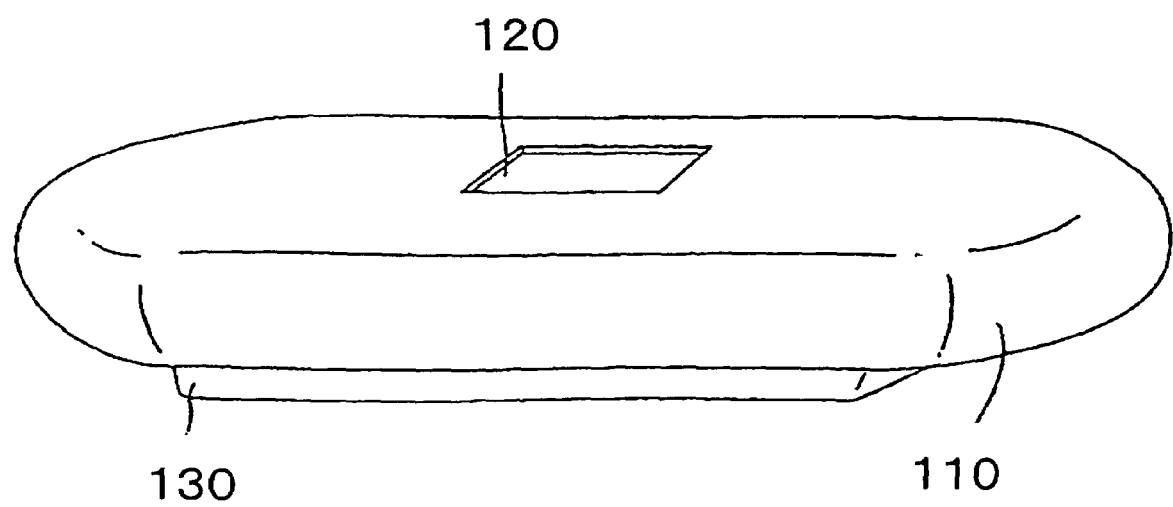
FIG. 5 is a perspective view illustrating an external view of an implantable, saccharide-measuring sensor according to the present invention.

An external view of an implantable, saccharide-measuring sensor according to the present invention is shown as a perspective view in FIG. 5. The implantable, saccharide-measuring sensor has a housing 110 for keeping liquid-tight the inside of the sensor, a window 120 for exposing only the optical isolation layer or the detector layer, and an antenna portion 130 for performing communications with a system arranged outside the body.

Figure 6:
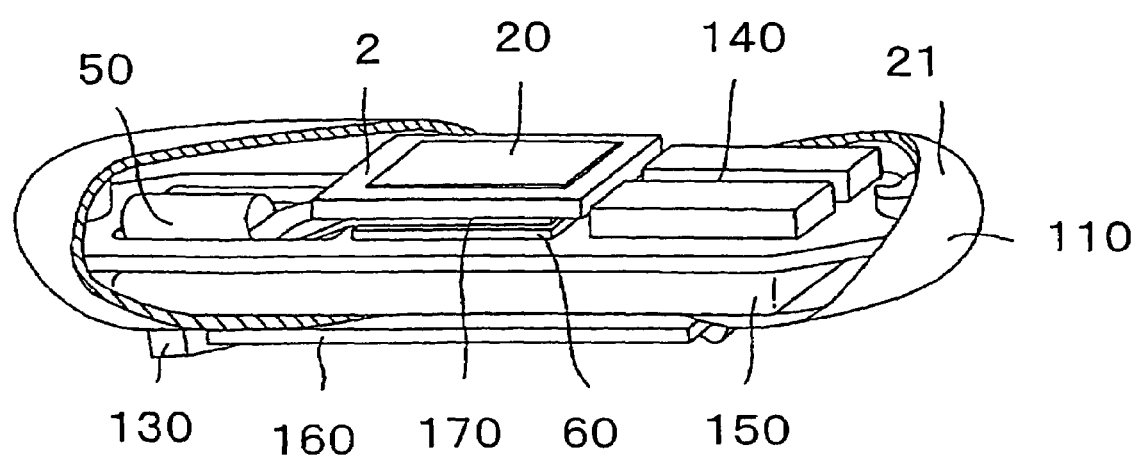
FIG. 6 is a perspective view depicting the internal structure of the implantable, saccharide-measuring sensor.

The internal structure of the implantable, saccharide-measuring sensor is depicted in FIG. 6. The optical isolation layer 20 or the detector layer 10 is arranged such that the window 120 is closed to keep the inside liquid-tight. Also mounted are the light source 50 for emitting excitation light, an optical waveguide path 170 for guiding light from the light source 50 to the detector layer 10, the fluorescence detector 60 for detecting fluorescence from the detector layer 10, an integrated circuit 140 for processing signal data from the fluorescence detector 60, and a battery 150 as an internal power supply. On the antenna portion 130, an antenna coil 160 is arranged. It is, however, to be noted that FIG. 5 and FIG. 6 are concept views, and implementations of the present invention shall not be limited to these figures. The size, shape and arrangement of each component can be determined freely as needed.

The use of the implantable, saccharide-measuring sensor makes it possible to avoid cumbersomeness and the occurrence of time lags in a continuous blood-sugar measurement when a diabetic controls the blood sugar level by himself or herself. In addition, the use of the implantable, saccharide-measuring sensor also allows a non-diabetic person to simply and easily perform blood sugar level measurements for health care.

The present invention will hereinafter be described specifically based on examples. It should, however, be borne in mind that the following examples by no means limit the present invention.

EXAMPLE 1

Synthesis of 9,10-bis[[N-methyl-N-(ortho-boronobenzyl)amino]methyl]anthracene-2-carboxylic acid-1-(6-acrylamido-n-hexyl)amide (hereinafter referred to as "F-AAm")

A) Synthesis of methyl 9,10-bis(bromomethyl)anthracene-2-carboxylate

Methyl 9,10-dimethylanthracene-2-carboxylate (360 mg), N-bromosuccinimide (540 mg) and benzoyl peroxide (5 mg) were added to a mixture of chloroform (4 mL) and carbon tetrachloride (10 mL), followed by heating under reflux for 2 hours. Subsequent to the removal of the solvent, the residue was extracted with methanol to afford the target compound (430 mg).

B) Synthesis of methyl 9,10-bis(aminomethyl)anthracene-2-carboxylate

Methyl 9,10-bis(bromomethyl)anthracene-2-carboxylate (400 mg) obtained in the above procedure A) was dissolved in chloroform (60 mL), a 2 M solution of methylamine in methanol (8 mL) was added, and the resulting mixture was stirred at room temperature for 4 hours. Subsequent to the removal of the solvent, the reaction product was purified on a silica gel column with methanol/chloroform as an eluent to afford the target compound (235 mg).

C) Synthesis of 9,10-bis[[N-methyl-N-(ortho-boronobenzyl)amino]methyl]anthracene-2-carboxylic acid Methyl 9,10-bis(aminomethyl)anthracene-2-carboxylate (200 mg) obtained in the above procedure (B), 2-(2-bromomethylphenyl)-1,3-dioxaborinane (700 mg) and N,N-diisopropylethylamine (0.35 mL) were dissolved in dimethylformamide (3 mL), followed by stirring at room temperature for 16 hours. Subsequent to removal of the solvent, the reaction product was purified on a silica gel column with methanol/chloroform as an eluent to afford the methyl ester (194 mg) of the target compound. The methyl ester was dissolved in methanol (5 mL), and 4 N sodium hydroxide (1 mL) was then added, followed by stirring at room temperature for 10 hours. The reaction mixture was neutralized with hydrochloric acid, and the inorganic salt was removed by gel filtration to afford the target compound (180 mg). The melting point of the reaction product was 121° C., and in DMSO-d6, it gave the following 1H-NMR data (δ, ppm): 2.15 ppm (d, 6H, N—CH3), 4.10 ppm (m, 4H, N—CH2-benzene), 4.45 ppm (m, 4H, N—CH2-anthracene), 7.55-8.90 ppm (m, 15H, aromatic).

D) Synthesis of F-AAm

In dimethylformamide (5 mL) with N,N-diisopropyl ethylamine (50 mg) contained therein, 9,10-Bis[[N-methyl-N-(ortho-boronobenzyl)amino]methyl]anthracene-2-carboxylic acid (70 mg) obtained in the above procedure C), 1-acrylamido-6-aminohexane (22 mg) and 1-[3-(dimethylamino)propyl]-3-ethylcarbodiimide (50 mg) were dissolved, followed by stirring at 60° C. for 18 hours. The reaction mixture was dissolved in chloroform (50 mL). The thus-prepared solution was washed three times with distilled water and once with saturated saline solution. The chloroform layer was dried with anhydrous sodium sulfate, and was then distilled to dryness under reduced pressure to afford the target compound (85 mg).

EXAMPLE 2

Synthesis of 9,10-bis[[N-methyl-N-(ortho-boronobenzyl)amino]methyl]anthracene-2-carboxylic acid-(terminal acrylamido-PEG3400)amide 9,10-Bis[[N-methyl-N-(ortho-boronobenzyl)amino]methyl]anthracene-2-carboxylic acid (10 mg) obtained in the above procedure C) of Example 1, amino-PEG3400-acrylamide (product of Nektar Corp.; 50 mg) and 1-[3-(dimethylamino)propyl]-3-ethylcarbodiimide (22 mg) were dissolved in 100 mM phosphate buffer (pH 6.0; 3 mL), followed by stirring at 60° C. for 24 hours. The reaction mixture was subjected to gel filtration, and a fluorescent polymer fraction was collected to afford the target compound (36 mg).

EXAMPLES 3 TO 9

Prepared were a dimethylsulfoxide (hereinafter referred to as "DMSO") solution having an F-AAm concentration of 10 wt %, a 80 wt % DMSO-water mixed solution having an acrylamide (hereinafter referred to as "AAm") concentration of 30 wt %, a 50 wt % DMSO-water mixed solution having a sodium persulfate (hereinafter referred to as "SPS") concentration of 3 wt %, and a DMSO solution having an N,N,N',N'-tetramethylethylenediamine (hereinafter abbreviated as "TEMED") concentration of 2 wt %. Using those reagent solutions, DMSO and water, reaction solutions were prepared to give their final concentrations and compositions as shown in Table 1. The thus-prepared reaction solutions were subjected to polymerization at room temperature for 2 hours to obtain copolymers of F-AAM and AAm. They will be referred to as Examples 3-9, respectively. The resultant copolymers were separately caused to precipitate from acetone, dissolved in water, and reprecipitated from acetone. This procedure was repeated twice to conduct purification. Subsequent to the purification, the resulting fluorescence sensor substances were dried in vacuo.

TABLE 1

|  | F-AAm (wt %) | AAm (wt %) | SPS (wt %) | TEMED (wt %) | DMSO (wt %) | Total amount (mL) | F-AAm/AAm Charged molar ratio |
|---|---|---|---|---|---|---|---|
| Example 3 | 1.46 | 2.1 | 0.15 | 0.04 | 80 | 2.0 | 1/14 |
| Example 4 | 0.43 |  |  |  |  |  | 1/50 |
| Example 5 | 0.15 |  |  |  |  |  | 1/144 |
| Example 6 | 0.10 |  |  |  |  |  | 1/215 |
| Example 7 | 0.050 |  |  |  |  |  | 1/430 |
| Example 8 | 0.015 |  |  |  |  |  | 1/1435 |
| Example 9 | 0.0075 |  |  |  |  |  | 1/2870 |

EXAMPLE 10

Production of 9,10-bis[[N-methyl-N-(ortho-boronobenzyl)amino]methyl]anthracene-2-carboxylic acid-(terminal acrylamido-PEG3400)amide/AAm copolymer Prepared were an aqueous solution with 9,10-bis[[N-methyl-N-(ortho-boronobenzyl)amino]methyl]anthracene-2-carboxylic acid-(terminal acrylamido-PEG3400)amide contained at 10 wt %, an aqueous solution with AAm contained at 30 wt %, a water mixed solution with SPS contained at 3 wt %, and an aqueous solution with TEMED contained at 2 wt %. With those reagent solutions, and water, a reaction solution was prepared containing a fluorescent monomer compound, which was the same as that synthesized in Example 2, at 0.6 wt %, AAm at 4.5 wt %, SPS at 0.3 wt % and TEMED at 0.08 wt %, all as final concentrations (1/427 in terms of the charged molar ratio of the fluorescent monomer compound to AAm). The reaction solution was subjected to polymerization at room temperature for 8 hours to afford a copolymer. The copolymer was caused to separately precipitate from acetone, dissolved in water, and reprecipitated from acetone. This procedure was repeated ten times to conduct purification. Subsequent to the purification, the resulting fluorescence sensor substance was dried in vacuo.

EXAMPLE 11

The copolymers obtained in Examples 3 to 10 were each dissolved in a 1/2 (v/v) solution of methanol and phosphate buffer to give a concentration of 0.05 mg/mL. Using a spectrophotometer, the absorbance at 265 nm was measured. Concerning an acrylamide homopolymer (molecular weight: 150,000), the absorbance was also measured likewise. This absorbance was subtracted, as a BLANK value, from the absorbance values of the copolymers of the respective examples.

Based on calibration curves prepared beforehand for the respective fluorescent monomer compounds, the fluorescent monomer compound/AAm ratios of the individual fluorescence sensor substances were determined. The results are shown in Table 2.

It is appreciated from Table 2 that in Example 3 to 9, the absorbance increased in proportion to the content of charged F-AAm and hence, F-AAm was incorporated at a fixed rate as a component as the respective fluorescence sensor substances.

TABLE 2

| | Fluorescent monomer compound/ AAm Charged molar ratio | Absorbance | Blank-corrected absorbance | Fluorescent monomer compound/ AAm Measured molar ratio |
|---|---|---|---|---|
| Example 3 | 1/14 | 0.725 | 0.698 | 1/10 |
| Example 4 | 1/50 | 0.231 | 0.204 | 1/59 |
| Example 5 | 1/144 | 0.113 | 0.086 | 1/185 |
| Example 6 | 1/215 | 0.076 | 0.049 | 1/282 |
| Example 7 | 1/430 | 0.052 | 0.025 | 1/572 |
| Example 8 | 1/1435 | 0.035 | 0.008 | 1/1932 |
| Example 9 | 1/2870 | 0.031 | 0.004 | 1/3874 |
| Example 10 | 1/427 | 0.032 | 0.005 | 1/3534 |

Calibration curve formula for fluorescent monomer compounds: y=20.158x (r=1, x: F-AAm concentration[μmol/mL])

EXAMPLE 12

Figure 7:
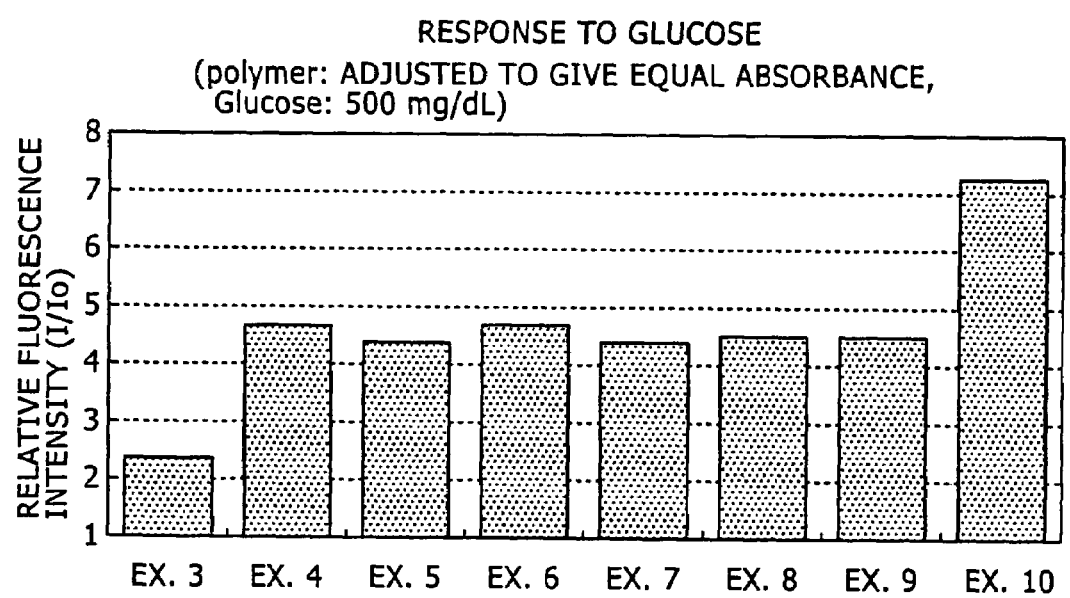
FIG. 7 is a chart showing glucose responses of fluorescence sensor substances of Examples 3-10.

To study the responses of the fluorescent monomer compounds in the copolymers, which had been synthesized in Examples 3 to 10, in fluorescence intensity to a glucose concentration by making equal the concentrations of the copolymers, the copolymers were each dissolved in phosphate buffer of pH 7.0 to give a concentration such that the absorbance at 265 nm would become 0.05. As shown in FIG. 7, among the relative fluorescence intensitys (Ex=405 nm, Em=442 nm) of the individual fluorescence sensor substance solutions at a glucose concentration of 500 mg/dL, the relative fluorescence intensity of the fluorescence sensor substance (F-AAm/AAm=1/14) of Example 3 was lower compared with those of the fluorescence sensor substances of the same F-AAm/AAm copolymer system. On the other hand, the fluorescence sensor substance of Example 10, which had been synthesized using the fluorescence monomer compound with the extended "Y" moiety contained therein, showed very high relative fluorescence intensity.

EXAMPLE 13

Figure 8:
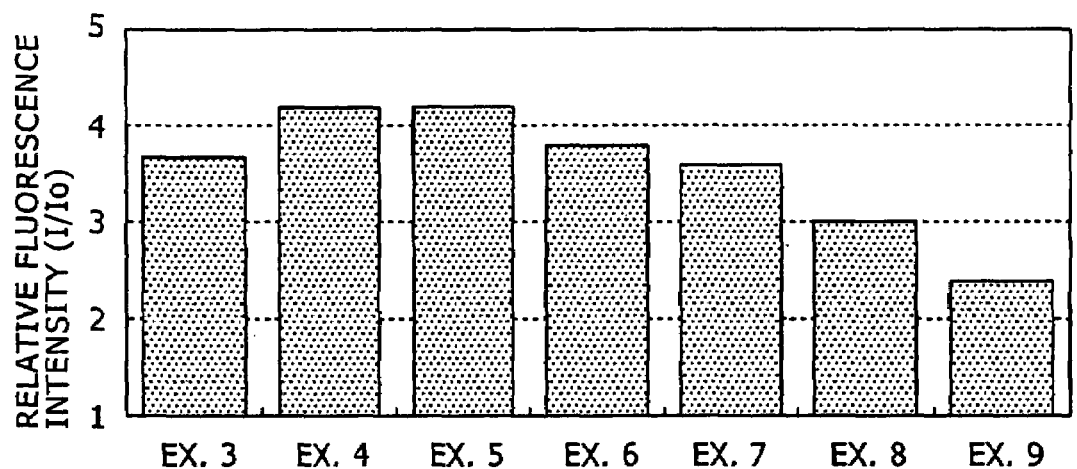
FIG. 8 is a chart showing glucose responses of fluorescence sensor substances of Examples 3-9.

The responses in fluorescence intensity to the glucose concentration of 500 mg/dL were studied in a similar manner as in Example 12 except that the concentrations of the copolymers synthesized in Examples 3 to 9 were adjusted equally at 10 μg/mL. The results are shown in FIG. 8.

EXAMPLE 14

A solution was prepared by dissolving and mixing AAm, N,N'-methylenebisacrylamide (hereinafter referred to as "BIS"), SPS, TEMED and F-AAm reagent solutions in an 80 wt % DMSO-water solution to give the following final concentrations: AAm: 15 wt %, BIS: 0.15 wt %, SPS: 0.3 wt %, TEMED: 0.08 wt %, and F-AAm: 0.50 wt % (F-AAm/AAm=1/300 in terms of the charged molar ratio).

A glass plate, which had been subjected beforehand to surface treatment with a silane coupling agent, and an untreated glass plate were arranged with a space left therebetween. The solution was poured into the space, followed by polymerization at room temperature for 2 hours under a nitrogen atmosphere. Subsequent to the completion of the polymerization, the glass plates were dipped in pure water, and only the untreated glass plate was separated to obtain a gel sheet formed of an F-AAm/AAm copolymer immobilized on the glass-made support material. The thus-obtained gel sheet was alternately dipped in methanol and 50 mM phosphate buffer (pH=7.0) thrice for 5 minutes per dip, and was then immersed and washed for 10 hours or longer in phosphate buffer to obtain a detector layer.

EXAMPLE 15

In dimethylformamide (30 mL) with N,N-diisopropylethylamine (0.2 mL) contained therein, 9,10-bis[[N-methyl-N-(ortho-boronobenzyl)amino]methyl]anthracene-2-carboxylic acid (350 mg) synthesized in the procedure C) of Example 1, methyl 6-aminohexanoate (200 mg) and 1-[3-(dimethylamino)propyl]-3-ethylcarbodiimide (220 mg) were dissolved, followed by stirring at room temperature for 4 hours. The reaction mixture was dissolved in chloroform (100 mL). The thus-prepared solution was washed three times with distilled water and once with saturated saline solution. The chloroform layer was dried with anhydrous sodium sulfate, and was then distilled to dryness under reduced pressure to afford its methyl ester (360 mg) as an intermediate. The intermediate was dissolved in methanol (10 mL), and subsequent to the addition of a 4 N aqueous solution of sodium hydroxide (1 mL), they were reacted at room temperature for 15 hours. The reaction mixture was loaded on an ion exchange column to remove the alkali, and was then concentrated to dryness to afford 9,10-bis[[N-methyl-N-(ortho-boronobenzyl)amino]methyl]anthracene-2-carboxylic acid-1-(6'-carboxylic acid-n-hexyl)amide (310 mg).

EXAMPLE 16

An aqueous solution of perchloric acid (effective chlorine concentration: 5 wt %, 8 g) and a 6 N aqueous solution of sodium hydroxide (30 mL) were taken in a shallow square stainless-steel container of 10 cm×10 cm, and then chilled to 0° C. A polyacrylamide membrane, which had been cut into a square of 10 cm×10 cm, was gently placed in the container, and was reacted at 0° C. for 2 hours. The reaction mixture was removed, and the resulting membrane was gently washed 4 times with distilled water (40 mL, each) and twice with dimethylformamide (20 mL, each) to obtain an activated polyacrylamide membrane.

9,10-Bis[[N-methyl-N-(ortho-boronobenzyl)amino]methyl]anthracene-2-carboxylic acid-1-(6'-carboxylic acid-n-hexyl)amide (20 mg), the fluorescent monomer compound synthesized in Example 15, 1-[3-(dimethylamino)propyl]-3-ethylcarbodiimide (12 mg) and 1-hydroxybenzotriazole (8 mg) were dissolved in dimethylformamide (10 mL). The resulting solution was poured into a shallow square stainless-steel container of 10 cm×10 cm, and the activated polyacrylamide membrane prepared in the above-described reaction was soaked. After the membrane was reacted at room temperature for 17 hours, it was washed thrice with dimethylformamide (20 mL, each), twice with 0.01 N hydrochloric acid (40 mL, each) and thrice with distilled water (40 mL, each), and further, was immersed and washed for 10 hours or longer in 50 mM phosphate buffer (pH=7.0) to obtain a detector layer with the fluorescent monomer compound immobilized on the polyacrylamide membrane.

Dextran (7 g) was dissolved at 50° C. under stirring in distilled water (175 mL), and subsequent to the addition of carbon black (5 g), the resulting mixture was subjected to ultrasonication until the carbon black was evenly dispersed. To the mixture, a 50 wt % aqueous solution of sodium hydroxide (3.5 mL) and ethylene glycol diglycidyl ether (6.5 g) were added, followed by stirring at 45° C. for 30 minutes. Distilled water (230 mL) was then added, and the resulting mixed solution was placed in a sprayer. The detector layer prepared in the preceding step was held in place on a flat glass plate, the mixed solution was sprayed evenly, and then, drying was conducted for 30 minutes in an oven controlled at 45° C. to obtain the detector layer with an optical isolation layer laminated thereon.

Comparative Example 1

Synthesis and Polymerization of 9,10-bis(methylene)[N-(acryloylaminohexyl)-N-(ortho-boronobenzyl)methylene]anthracene (hereinafter referred to as "F-AAm-2")

A') Synthesis of 9,10-bis[6'-(t-butoxycarbonylamino)hexylaminomethyl]anthracene 9,10-Bis(chloromethyl)anthracene (500 mg), N—BOC-hexyldiamine (1.3 g) and diisopropylethylamine (1.25 mL) were dissolved in dimethyl sulfoxide (10 mL), followed by reaction under stirring at 60° C. for 6 hours. The reaction mixture was diluted with chloroform (60 mL), and washed thrice with water (100 mL, each) and once with saturated saline solution (100 mL). The organic layer was dried over anhydrous sodium sulfate. After the desiccant was filtered off, the organic layer was concentrated, and the concentrate was purified by chromatography on a silica gel column with chloroform/methanol as an eluent to afford the target compound (56 mg).

B') Synthesis of 9,10-bis[[N-6'-(t-butoxycarbonylamino)hexyl-N-[2-(5,5-dimethylborinan-2-yl)benzyl]amino]methyl]anthracene The product (50 mg) obtained in the above procedure A'), 2-(2-bromomethylphenyl)-1,3-dioxaborinane (170 mg) and N,N-diisopropylethylamine (0.1 mL) were dissolved in dimethylformamide (1 mL), followed by stirring at 25° C. for 5 hours. Subsequent to the removal of the solvent, the reaction product was purified on a silica gel column with methanol/chloroform as an eluent to afford the target compound (35 mg).

C') Synthesis of 9,10-bis[[N-6'-aminohexyl-N-(ortho-boronobenzyl)amino]methyl]anthracene The product (35 mg) obtained in the above procedure B') was dissolved in methanol (1 mL). 4 N hydrochloric acid (0.5 mL) was added, and the thus-obtained mixture was stirred at 25° C. for 10 hours. Subsequent to evaporation to dryness, the inorganic salt was removed by gel filtration to afford the target compound (26 mg).

D') Synthesis of F-AAm-2

The product (25 mg) obtained in the above procedure C') was dissolved in DMF (0.5 mL). Under a nitrogen atmosphere, N,N-diisopropylethylamine (20 mg) and acryloyl chloride (12 mg) were added at −10° C., followed by reaction under stirring for 30 minutes. The reaction mixture was poured into iced water, extracted with chloroform, and washed with saturated saline solution. The chloroform layer was dried, and was then evaporated to dryness to afford the target product represented by the below-described formula (11) (26 mg) as a comparative compound.

E') Polymerization

A solution was prepared by dissolving and mixing AAm monomer, BIS, SPS, TEMED and F-AAm-2 represented by the formula (11) in an 80 wt % DMSO-water solution to give the following final concentrations: AAm monomer: 15 wt %, BIS: 0.15 wt %, SPS: 0.3 wt %, TEMED: 0.08 wt %, and F-AAm-2: 0.50 wt % (F-AAm-2/AAm=1/300 in terms of the charged molar ratio).

A glass plate, which had been subjected beforehand to surface treatment with a silane coupling agent, and an untreated glass plate were arranged with a space left therebetween. The solution was poured into the space, followed by polymerization at room temperature for 2 hours under a nitrogen atmosphere. Subsequent to the completion of the polymerization, the glass plates were dipped in pure water, and only the untreated glass plate was separated to obtain a gel sheet formed of an F-AAm-2/AAm copolymer immobilized on the glass-made support material. The thus-obtained gel sheet was alternately dipped in methanol and 50 mM phosphate buffer (pH=7.0) thrice for 5 minutes per dip, and was then immersed and washed for 10 hours or longer in phosphate buffer to obtain a detector layer preform. An optical isolation layer was laminated on the detector layer preform in a similar manner as in Example 16 to provide a detector layer.

Formula (11)

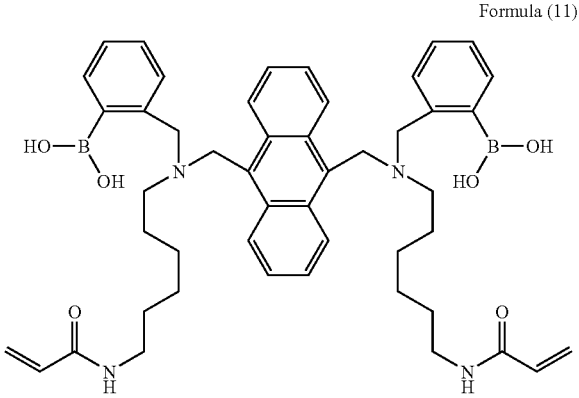

EXAMPLE 17

Synthesis of 9,10-bis(methylene)[[N-(ortho-boronobenzyl)methylene]-N-[(acryloylpolyoxyethylene)carbonylamino]-n-hexamethylene]-2-acetylanthracene (hereinafter referred to as "F-PEG-AAm-1")

A) Synthesis of 9,10-bis(bromomethyl)-2-acetylanthracene 9,10-Dimethyl-2-acetylanthracene (600 mg), N-bromosuccinimide (800 mg) and benzoyl peroxide (5 mg) were added to a mixture of chloroform (6 mL) and carbon tetrachloride (20 mL), followed by heating under reflux at 80° C. for 2 hours. After the solvent was eliminated, the residue was extracted with methanol to afford the target compound (780 mg).

B) Synthesis of 9,10-bis[6'-(t-butoxycarbonylamino)hexylaminomethyl]-2-acetylanthracene The product (500 mg) obtained in the above procedure A), N-BOC-hexyldiamine (1.125 g) and diisopropylethylamine (1.25 mL) were dissolved in dimethylformamide (10 mL), followed by reaction under stirring at 45° C. for 1 hour. The reaction mixture was diluted with chloroform (60 mL), and then washed thrice with water (100 mL, each) and once with saturated saline solution (100 mL). The organic layer was dried over anhydrous sodium sulfate. After the desiccant was filtered off, the organic layer was concentrated, and the concentrate was purified by chromatography on a silica gel column with chloroform/methanol as an eluent to afford the target compound (367 mg).

C) Synthesis of 9,10-bis[[N-6'-(t-butoxycarbonylamino) hexyl-N-[2-(5,5-dimethylborinan-2-yl)benzyl]amino]methyl]-2-acetylanthracene The product (200 mg) obtained in the above procedure B), 2-(2-bromomethylphenyl)-1,3-dioxaborinane (700 mg) and N,N-diisopropylethylamine (0.35 mL) were dissolved in dimethylformamide (3 mL), followed by stirring at 25° C. for 16 hours. Subsequent to the removal of the solvent, the reaction product was purified on a silica gel column with methanol/chloroform as an eluent to afford the target compound (194 mg).

D) Synthesis of 9,10-bis[[N-6'-aminohexyl-N-(ortho-boronobenzyl)amino]methyl]-2-acetylanthracene The product (100 mg) obtained in the above procedure C) was dissolved in methanol (2 mL). 4 N hydrochloric acid (2 mL) was added, and the thus-obtained mixture was stirred at 25° C. for 10 hours. Subsequent to evaporation to dryness, the inorganic salt was removed by gel filtration to afford the target compound (95 mg).

E) Synthesis of F-PEG-AAm-1

The product (160 mg) obtained in the above procedure D) was dissolved in dimethylformamide (0.5 mL). The solution was added to a solution of acryloyl-(polyethylene glycol)-N-hydroxysuccinimide ester (PEG molecular weight: 3,400; 1.22 g) in 100 mM phosphate buffer (pH=8.0; 10 mL), followed by stirring at 25° C. for 20 hours. The reaction mixture was subjected to gel filtration to collect a fluorescent macromolecule fraction. Subsequent to lyophilization, the target compound was obtained (1.2 g). The above procedures A) to E) are shown in the synthesis scheme of FIG. 1. F-PEG-AAm-1 was dissolved at 100 mM concentration in water under the conditions of 25° C. temperature and pH 7.0 without the presence of any organic solvent or solubilizer. The 1H-NMR data of the target compound in deuterochlorofomm were as follows (δ, ppm): 1.30-1.65 (m, C—CH2-C), 2.90 (s, Ac), 2.78 (m, —C(=C)N—CH2-C), 3.25 (m, CH2-NH—COO), 3.50-3.80 (s, PEG), 5.80 (d, COCH=C), 6.17 (m, C=CH2), 7.20-8.20 (m, aromatic). No hydrogen signal was confirmed to overlap a peak ascribable to PEG residual groups.

EXAMPLE 18

A solution was prepared by dissolving and mixing acrylamide, F-PEG-AAm-1 synthesized in Example 17, methylene-bisacrylamide, sodium persulfate and N,N,N',N'-tetramethylethylenediamine in pure water to give the following final concentrations: acrylamide: 15 wt %, F-PEG-AAm-1: 10 wt %, methylene-bisacrylamide: 0.3 wt %, sodium persulfate: 0.18 wt %, and N,N,N',N'-tetramethylethylenediamine: 0.36 wt %. A glass plate, which had been subjected beforehand to surface treatment with a silane coupling agent, and an untreated glass plate were arranged with a space left therebetween. The solution was poured into the space, followed by polymerization at 25° C. for 8 hours under a nitrogen atmosphere. Subsequent to the completion of the polymerization, the glass plates were dipped in pure water, and only the untreated glass plate was separated to obtain a gel sheet formed of an acrylamide/F-PEG-AAm-1 (molar ratio: 160/1) copolymer immobilized on the glass-made support material.

A solution was prepared by dissolving or mixing acrylamide, methylene-bisacrylamide, sodium persulfate, N,N,N', N'-tetramethylethylenediamine and carbon black in pure water to give the following final concentrations: acrylamide: 20 wt %, methylene-bisacrylamide: 1 wt %, sodium persulfate: 0.18 wt %, N,N,N',N'-tetramethylethylenediamine: 0.36 wt %, and carbon black: 5 wt %. The solution was applied to a surface of the gel sheet, followed by polymerization at 25° C. for 24 hours under a nitrogen atmosphere. The resulting gel sheet was dipped and washed ten times in total for 30 minutes per dip in 50 mM phosphate buffer (pH 7.0) having a glucose concentration of 500 mg/dL. Subsequently, the gel sheet was dipped and washed 4 times in total for 30 minutes per dip in 50 mM phosphate buffer (pH 7.0) such that glucose was washed off to obtain a detector layer.

EXAMPLE 19

Synthesis of methyl 9,10-bis(methylene)[[N-(ortho-boronobenzyl)]-N-[(acryloylpolyoxyethylene)carbonylamino]-n-hexamethylene]-anthracene-2-carboxylate (Hereinafter Referred to as "F-PEG-AAm-2")

a) Synthesis of 9,10-dimethylanthracene-2-carboxylic acid 9,10-Dimethyl-2-acetylanthracene (1.2 g) was dissolved in dioxane (24 mL). An aqueous solution of sodium perchlorate (10 mL; effective chlorine concentration: 10 wt %) was then added, followed by reaction under stirring at 85° C. for 8 hours. The reaction mixture was chilled, and then rendered acidic with dilute hydrochloric acid. The resulting precipitate was collected by filtration, washed with a small amount of water, and then dried in vacuo to afford the target compound (1.16 g).

b) Synthesis of methyl 9,10-dimethylanthracene-2-carboxylate

The product (1 g) obtained in the above procedure a) was dissolved in 5 wt % hydrochloric acid-methanol, followed by heating under reflux for 20 hours. The reaction mixture was concentrated, and water (30 mL) was added. The resulting mixture was extracted with chloroform (100 mL). The chloroform layer was washed with an aqueous solution of sodium bihydrogencarbonate and saturated saline solution, and was then dried over anhydrous sodium sulfate. The chloroform layer was evaporated to dryness to afford the target compound (915 mg).

c) Synthesis of methyl 9,10-bis(bromomethylene)anthracene-2-carboxylate

The product (600 mg) obtained in the above procedure b), N-bromosuccinimide (800 mg) and benzoyl peroxide (5 mg) were added to a mixture of chloroform (6 mL) and carbon tetrachloride (20 mL), followed by heating under reflux for 2 hours. Subsequent to the removal of the solvent, the residue was extracted with methanol to afford the target compound (767 mg).

d) Synthesis of methyl 9,10-bis[6'-(t-butoxycarbonylamino)hexylaminomethyl]anthracene-2-carboxylate The product (500 mg) obtained in the above procedure c), N-BOC-hexyldiamine (1.125 g) and diisopropylethylamine (1.25 mL) were dissolved in dimethylformamide (10 mL), followed by reaction under stirring at 45° C. for 2 hours. The reaction mixture was diluted with chloroform (60 mL), and then washed thrice with water (100 mL, each) and once with saturated saline solution (100 mL). The organic layer was dried over anhydrous sodium sulfate. After the desiccant was filtered off, the organic layer was concentrated, and the concentrate was purified by chromatography on a silica gel column with chloroform/methanol as an eluent to afford the target compound (307 mg).

e) Synthesis of methyl 9,10-bis[[N-6'-(t-butoxycarbonylamino)hexyl-N-[2-(5,5-dimethylborinan-2-yl)benzyl]amino]methyl]anthracene-2-carboxylate The product (200 mg) obtained in the above procedure d), 2-(2-bromomethylphenyl)-1,3-dioxaborinane (700 mg) and N,N-diisopropylethylamine (0.35 mL) were dissolved in dimethylformamide (3 mL), followed by stirring at 25° C. for 16 hours. Subsequent to the removal of the solvent, the reaction product was purified on a silica gel column with methanol/chloroform as an eluent to afford the target compound (203 mg).

f) Synthesis of methyl 9,10-bis(methylene)[[N-(ortho-boronobenzyl)methylene]-N-(aminohexyl)]anthracene-2-carboxylate The product (100 mg) obtained in the above procedure e) was dissolved in methanol (3 mL). 8 N hydrochloric acid (0.5 mL) was added, and the thus-obtained mixture was stirred at 25° C. for 2 days. Subsequent to evaporation to dryness, the inorganic salt was removed by gel filtration to afford the target compound (82 mg).

g) Synthesis of F-PEG-AAm-2

The product (160 mg) obtained in the above procedure f) was dissolved in dimethylformamide (0.5 mL). The solution was added to a solution of acryloyl-(polyethylene glycol)-N-hydroxysuccinimide ester (PEG molecular weight: 3,400; 1.22 g) in 100 mM phosphate buffer (pH=8.0; 10 mL), followed by stirring at 25° C. for 20 hours. The reaction mixture was subjected to gel filtration to collect a fluorescent macromolecule fraction. Subsequent to lyophilization, the target compound was obtained (1.1 g). The above procedures a) to e) are shown in the synthesis scheme of FIG. 3. F-PEG-AAm-2 was dissolved at 100 mM concentration in water under the conditions of 25° C. temperature and pH 7.0 without the presence of any organic solvent or solubilizer. The 1H-NMR data of the target compound in deuterochloroform were as follows ($\delta$, ppm): 1.30-1.65 (m, C—$CH_2$—C), 2.78 (m, —C(—C)N—$CH_2$—C), 3.25 (m, $CH_2$—NH—COO), 3.50-3.80 (s, PEG), 4.10 (s, $COOCH_3$), 5.80 (d, COCH=C), 6.17 (m, C=$CH_2$), 7.20-8.20 (m, aromatic). No hydrogen signal was confirmed to overlap a peak ascribable to PEG residual groups.

EXAMPLE 20

Using F-PEG-AAm-2 synthesized in Example 19, a gel sheet formed of an acrylamide/F-PEG-AAm-2 (molar ratio: 160/1) immobilized on a glass-made support material was obtained in a similar manner as in Example 18. Further, a detector layer was obtained in a similar manner as in Example 18.

Comparative Example 2

Synthesis and Polymerization of AAm-2

F-AAm-2 represented by the formula (11) was synthesize in a similar manner as in the procedures A') to D') of Comparative Example 1.

E") Polymerization

A solution was prepared by dissolving and mixing acrylamide, methylene-bisacrylamide, F-AAm-2, sodium persulfate and N,N,N',N'-tetramethylethylenediamine in an 80 v/v % aqueous solution of dimethylsulfoxide to give the following final concentrations: acrylamide: 15 wt %, methylenebisacrylamide: 0.3 wt %, F-AAm-2: 1.2 wt %, sodium persulfate: 0.18 wt %, and N,N,N',N'-tetramethylethylenediamine: 0.36 wt %.

A glass plate, which had been subjected beforehand to surface treatment with a silane coupling agent, and an untreated glass plate were arranged with a space left therebetween. The solution was poured into the space, followed by polymerization at 25° C. for 8 hours under a nitrogen atmosphere. Subsequent to the completion of the polymerization, the glass plates were dipped in pure water, and only the untreated glass plate was separated to obtain a gel sheet formed of an acrylamide/F-AAm-2 (molar ratio: 150/1) copolymer immobilized on the glass-made support material.

A solution was prepared by dissolving or mixing acrylamide, methylene-bisacrylamide, sodium persulfate, N,N,N',N'-tetramethylethylenediamine and carbon black in pure water to give the following final concentrations: acrylamide: 20 wt %, methylene-bisacrylamide: 1 wt %, sodium persulfate: 0.18 wt %, N,N,N',N'-tetramethylethylenediamine: 0.36 wt %, and carbon black: 5 wt %. The solution was applied to a surface of the gel sheet, followed by polymerization at 25° C. for 24 hours under a nitrogen atmosphere. The resulting gel sheet was dipped and washed ten times in total for 30 minutes per dip in 50 mM phosphate buffer (pH 7.0) having a glucose concentration of 500 mg/dL. Subsequently, the gel sheet was dipped and washed 4 times in total for 30 minutes per dip in 50 mM phosphate buffer (pH 7.0) such that glucose was washed off to obtain a detector layer.

EXAMPLE 21

The detector layers obtained in Example 16 and Comparative Example 1 were held in place on evaluation devices, respectively. Under phosphate buffer (pH=7.0), their responses to glucose at varied concentrations were evaluated in fluorescence intensity. The results are shown in FIG. 9.

Each evaluation device was provided with a cell, a bundle of optical fibers, and a fluorospectrometer. The cell can fixedly accommodate the detector layer, and permits circulation of a liquid through the inside thereof. The bundle of optical fibers is fixedly secured at one end thereof on a rear side of the cell, and is connected at an opposite end thereof to the fluorospectrometer. A fraction of the bundled optical fibers is used to feed exciting light to the cell, and the remaining fraction of the bundled optical fibers is used to return fluorescent radiation from the cell.

Figure 9:
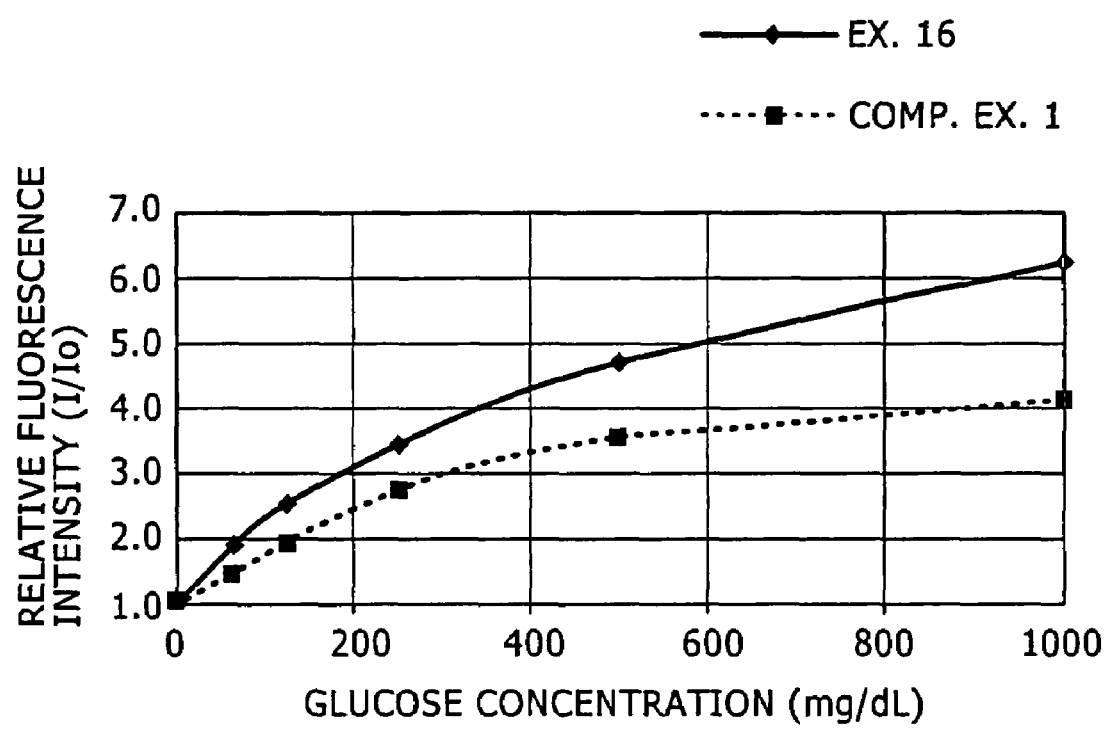
FIG. 9 is a chart showing glucose responses of detector layers of Example 16 and Comparative Example 1.

As clearly envisaged from FIG. 9, it is appreciated that the detector layer of Example 16 is superior in the response to glucose compared with the detector layer of Comparative Example 1.

EXAMPLE 22

Figure 10:
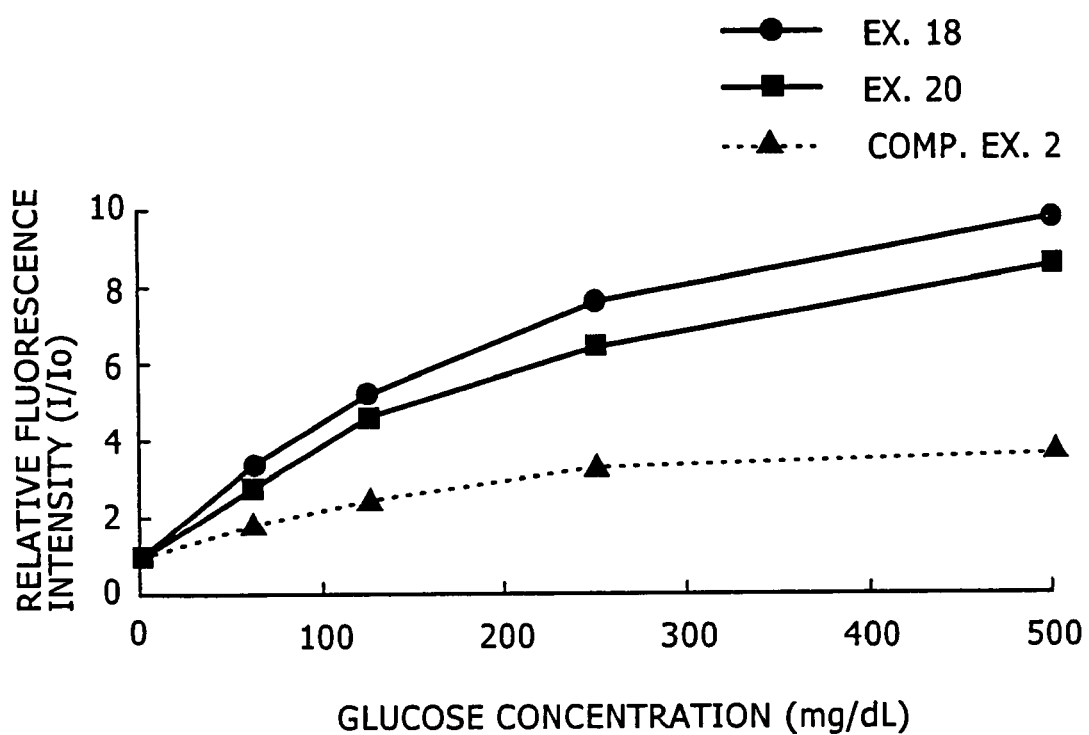
FIG. 10 is a chart showing glucose responses of detector layers of Example 18, Example 20 and Comparative Example 2.

The detector layers obtained in Example 18, Example 20 and Comparative Example 2 were held in place on evaluation devices, respectively. Under phosphate buffer (pH=7.0), their responses to glucose at varied concentrations were evaluated in fluorescence intensity. The results are shown in FIG. 10. The evaluation devices used were similar to those employed in Example 21.

As clearly envisaged from FIG. 10, it is evident that the detector layers of Examples 18 and 20, which had been produced using the water-soluble monomer, were superior in the response to glucose compared with the detector layer of Comparative Example 2 produced using the conventional hydrophobic monomer.

EXAMPLE 23

The detector layers obtained in Examples 16, 18 and 20 and Comparative Example 2 were held in place on evaluation devices, respectively. Under phosphate buffer (pH=7.0), fluorescent spectra were measured.

The detector layer of Comparative Example 2 showed maximum fluorescence wavelengths at 403 nm and 430 nm when excited at 377 nm. On the other hand, the detector layer of Example 16 showed a maximum fluorescence wavelength at 450 nm when excited at 400 nm, the detector layer of Example 18 showed a maximum fluorescence wavelength at 480 nm when excited at 400 nm, and the detector layer of Example 20 showed a maximum fluorescence wavelength at 455 nm when excited at 400 mm. Each detector layer according to the present invention has a fluorescent wavelength shifted toward the longer side, has a great difference between its excitation wavelength and fluorescence wavelength, is advantageous from the standpoint of fluorescence characteristics, and is expected to provide high measurement accuracy.

What is claimed is:

1. A fluorescence sensor substance comprising a compound represented by the following formula (7):

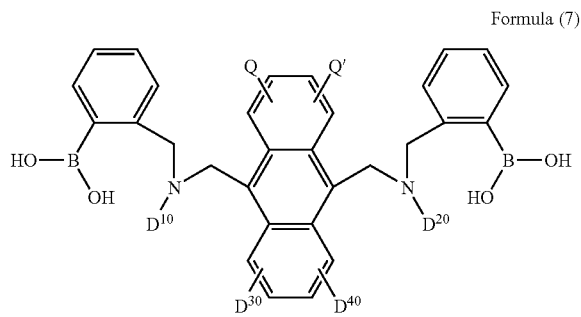

Formula (7)

wherein:
Q and Q' may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups;
and in $D^{10}$, $D^{20}$, $D^{30}$ and $D^{40}$,
(x) $D^{10}$ and $D^{20}$ may be the same or different and are each a substituted or unsubstituted alkyl group, $D^{30}$ is a hydrogen atom, and $D^{40}$ is a substituent group represented by the following formula (8), or
(xx) $D^{10}$ and $D^{20}$ may be the same or different and are each a substituent group represented by the following formula (9), and $D^{30}$ and $D^{40}$ may be the same or different, may be combined together into a fused ring, and are each a substituent selected from the group consisting of a hydrogen atom, a halogen atom, a hydroxyl group, and substituted or unsubstituted alkyl, acyl, oxyalkyl, carboxyl, carboxylate ester, carboxamido, cyano, nitro, amino and aminoalkyl groups:

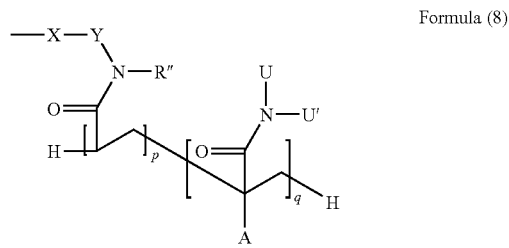

Formula (8)

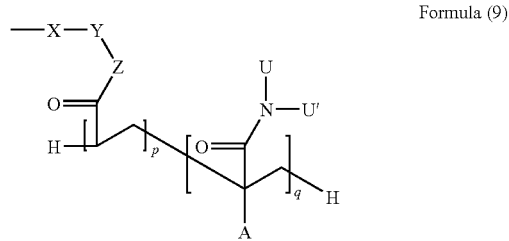

Formula (9)

wherein:
X, in a case of said definition (x), is a substituent group selected from the group consisting of —COO—, —OCO—, —CH$_2$NR—, —CH$_2$S—, —CH$_2$O—, —NR—, —NRCO—, —CONR—, —SO$_2$NR—, —NRSO$_2$—, —O—, —S—, —SS—, —NRCOO—, —OCONR— and —CO—, and in a case of said definition (xx), represents a C1 to C30 alkylene group containing at least one substituent group selected from the group consisting of —COO—, —OCO—, —CH$_2$NR—, —NR—, —NRCO—, —CONR—, —SO$_2$NR—, —NRSO$_2$—, —O—, —S—, —SS—, —NRCOO—, —OCONR— and —CO—, in which R represents a hydrogen atom or a substituted or unsubstituted alkyl group, Y comprises one or more of an amino group, carboxy group, sulfo group, nitro group, phosphate group, hydroxyl group, and/or a group comprising an ether, amide and/or ester linkage, Z represents —O— or —NR"—, R" represents a hydrogen atom or a substituted or unsubstituted alkyl group, A is a hydrogen atom or a methyl group, U and U' may be the same or different and are each a substituted or unsubstituted alkyl group, and wherein when $D^{10}$, $D^{20}$, $D^{30}$ and $D^{40}$ have the same meanings as defined under said definition (x), a molar ratio of p to q is from 1:100 to 1:2000, and wherein when $D^{10}$, $D^{20}$, $D^{30}$ and $D^{40}$ have the same meanings as defined under said definition (xx), a molar ratio of p to q is from 1:150 to 1:3000.

2. The fluorescence sensor substance according to claim 1, wherein Y comprises a structure represented by the following formula (4) or formula (5):

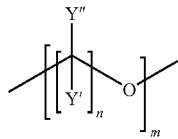

Formula (4)

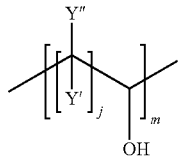

Formula (5)

wherein n is from 2 to 5, j is from 1 to 5, m is from 1 to 200, and Y' and Y" may be the same or different and are each a hydrogen atom or an alkyl group.

3. The fluorescence sensor substance according to claim 1, wherein $D^{10}$, $D^{20}$, $D^{30}$ and $D^{40}$ have the meanings as defined under said definition (x), and Y comprises one or more of an amino group, carboxy group, sulfo group, nitro group, phosphate group, hydroxyl group, and/or a group comprising an ether, amide and/or ester linkage, wherein Y has a number of atoms of from 3 to 500.

4. The fluorescence sensor substance according to claim 1, wherein at least a portion of said copolymer comprises intermolecular crosslinks formed therein, and has a three-dimensional crosslinked structure.

5. An implantable, glucose-measuring sensor comprising the fluorescence sensor substance as defined in claim 1.

* * * * *